(12) United States Patent
Plahey et al.

(10) Patent No.: US 8,784,359 B2
(45) Date of Patent: Jul. 22, 2014

(54) CASSETTE SYSTEM FOR PERITONEAL DIALYSIS MACHINE

(75) Inventors: Kulwinder S. Plahey, Martinez, CA (US); Frank L. Hedmann, Volkach (DE); Stephan Klatte, Wurzburg (DE); Thomas Irvin Folden, Alamo, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 282 days.

(21) Appl. No.: 13/092,560

(22) Filed: Apr. 22, 2011

(65) Prior Publication Data

US 2011/0196289 A1 Aug. 11, 2011

Related U.S. Application Data

(63) Continuation of application No. 11/515,359, filed on Aug. 31, 2006, now Pat. No. 7,935,074, which is a continuation-in-part of application No. 11/069,195, filed on Feb. 28, 2005, now abandoned.

(51) Int. Cl.
*A61M 1/28* (2006.01)
*A61M 1/16* (2006.01)

(52) U.S. Cl.
CPC . *A61M 1/28* (2013.01); *A61M 1/16* (2013.01); *A61M 2205/128* (2013.01)
USPC .............................................. 604/29; 417/395

(58) Field of Classification Search
CPC .... A61M 1/28; A61M 2205/128; A61M 1/16
USPC .................. 5/28–33, 131; 210/258, 646, 787; 604/29, 33, 67, 151
See application file for complete search history.

(56) References Cited

U.S. PATENT DOCUMENTS

| 2,383,193 A | 8/1945 | Herbert |
| 3,927,955 A | 12/1975 | Spinosa et al. |

(Continued)

FOREIGN PATENT DOCUMENTS

| DE | 198 37 667 | 3/2000 |
| DE | 19919572 A1 | 11/2000 |

(Continued)

OTHER PUBLICATIONS

Acumen, "Acute Dialysis Machine Brief Operating Instructions," Software Version 1.0, pp. 1-146.

(Continued)

*Primary Examiner* — Nicholas Lucchesi
*Assistant Examiner* — Gerald Landry, II
(74) *Attorney, Agent, or Firm* — Fish & Richardson P.C.

(57) ABSTRACT

A peritoneal dialysis (PD) system that includes a disposable PD cassette including a base having a substantially planar portion and a dome-shaped protrusion extending from the substantially planar portion and a flexible membrane attached to the base and covering a recessed region of the dome-shaped protrusion to form a pumping chamber between the flexible membrane and the recessed region of the dome-shaped protrusion. The system also includes a PD machine including a deck and a door hinged from one side to the deck. The door and the deck can cooperate to form a cassette compartment, and the door has a cylindrical recess positioned to receive the dome-shaped protrusion of the base of the disposable PD cassette when the disposable PD cassette is disposed in the cassette compartment and the door is closed.

12 Claims, 20 Drawing Sheets

(56) References Cited

U.S. PATENT DOCUMENTS

| | | |
|---|---|---|
| 3,966,358 A | 6/1976 | Heimes et al. |
| 3,985,135 A | 10/1976 | Carpenter et al. |
| 4,026,669 A | 5/1977 | Leonard et al. |
| 4,273,121 A | 6/1981 | Jassawalla |
| 4,303,376 A | 12/1981 | Siekmann |
| 4,370,983 A | 2/1983 | Lichtenstein |
| 4,382,753 A | 5/1983 | Archibald |
| 4,410,322 A | 10/1983 | Archibald |
| 4,436,620 A | 3/1984 | Bellotti et al. |
| 4,453,932 A | 6/1984 | Pastrone |
| 4,479,762 A | 10/1984 | Bilstad et al. |
| 4,486,189 A | 12/1984 | Troutner et al. |
| 4,569,378 A | 2/1986 | Bergandy |
| 4,623,328 A | 11/1986 | Hartranft |
| 4,628,499 A | 12/1986 | Hammett |
| 4,639,245 A | 1/1987 | Pastrone et al. |
| 4,643,713 A | 2/1987 | Viitala |
| 4,657,490 A | 4/1987 | Abbott |
| 4,662,906 A | 5/1987 | Matkovich et al. |
| 4,666,598 A | 5/1987 | Heath et al. |
| 4,676,467 A | 6/1987 | Palsulich |
| 4,710,166 A | 12/1987 | Thompson et al. |
| 4,716,520 A | 12/1987 | Locke et al. |
| 4,778,451 A | 10/1988 | Kamen |
| 4,798,090 A | 1/1989 | Heath et al. |
| 4,808,161 A | 2/1989 | Kamen |
| 4,826,482 A | 5/1989 | Kamen |
| 4,828,543 A | 5/1989 | Weiss et al. |
| 4,840,542 A | 6/1989 | Abbott |
| 4,842,584 A | 6/1989 | Pastrone |
| 4,902,282 A | 2/1990 | Bellotti et al. |
| 4,927,411 A | 5/1990 | Pastrone et al. |
| 4,950,134 A | 8/1990 | Bailey et al. |
| 4,976,162 A | 12/1990 | Kamen |
| 4,997,464 A | 3/1991 | Kopf |
| 5,002,471 A | 3/1991 | Perlov |
| 5,036,886 A | 8/1991 | Olsen et al. |
| 5,061,236 A | 10/1991 | Sutherland et al. |
| 5,088,515 A | 2/1992 | Kamen |
| 5,098,262 A | 3/1992 | Wecker et al. |
| 5,100,380 A | 3/1992 | Epstein et al. |
| 5,100,699 A | 3/1992 | Roeser |
| 5,116,021 A | 5/1992 | Faust et al. |
| 5,116,316 A | 5/1992 | Sertic et al. |
| 5,146,713 A | 9/1992 | Grafius |
| 5,151,019 A | 9/1992 | Danby et al. |
| 5,167,837 A | 12/1992 | Snodgrass et al. |
| 5,171,029 A | 12/1992 | Maxwell et al. |
| 5,178,182 A | 1/1993 | Kamen |
| 5,187,990 A | 2/1993 | Magnussen et al. |
| 5,193,990 A | 3/1993 | Kamen et al. |
| 5,211,201 A | 5/1993 | Kamen et al. |
| 5,241,985 A | 9/1993 | Faust et al. |
| 5,247,434 A | 9/1993 | Peterson et al. |
| 5,250,027 A | 10/1993 | Lewis et al. |
| 5,252,044 A | 10/1993 | Raines et al. |
| 5,279,556 A | 1/1994 | Goi et al. |
| 5,302,093 A | 4/1994 | Owens et al. |
| 5,311,908 A * | 5/1994 | Barone et al. ............... 137/881 |
| 5,315,632 A * | 5/1994 | Flynn et al. ............... 378/167 |
| 5,324,422 A | 6/1994 | Colleran et al. |
| 5,330,425 A | 7/1994 | Utterberg |
| 5,350,357 A | 9/1994 | Kamen et al. |
| D351,470 S | 10/1994 | Scherer et al. |
| 5,353,837 A | 10/1994 | Faust |
| 5,395,351 A | 3/1995 | Munsch |
| 5,415,528 A | 5/1995 | Ogden et al. |
| 5,421,208 A | 6/1995 | Packard et al. |
| 5,421,823 A | 6/1995 | Kamen et al. |
| 5,427,509 A | 6/1995 | Chapman et al. |
| 5,431,626 A | 7/1995 | Bryant et al. |
| 5,431,627 A | 7/1995 | Pastrone et al. |
| 5,431,634 A | 7/1995 | Brown |
| 5,438,510 A | 8/1995 | Bryant et al. |
| 5,441,636 A | 8/1995 | Chevallet et al. |
| 5,445,506 A | 8/1995 | Afflerbaugh et al. |
| 5,447,286 A | 9/1995 | Kamen et al. |
| 5,450,743 A | 9/1995 | Buote |
| 5,462,416 A | 10/1995 | Dennehey et al. |
| 5,462,417 A | 10/1995 | Chapman |
| 5,474,683 A | 12/1995 | Bryant et al. |
| 5,478,211 A | 12/1995 | Dominiak et al. |
| 5,480,294 A | 1/1996 | Di Perna et al. |
| 5,482,438 A | 1/1996 | Anderson et al. |
| 5,482,440 A | 1/1996 | Dennehey et al. |
| 5,482,446 A | 1/1996 | Williamson et al. |
| 5,484,239 A | 1/1996 | Chapman et al. |
| 5,486,286 A | 1/1996 | Peterson et al. |
| 5,514,069 A | 5/1996 | Brown et al. |
| 5,514,102 A | 5/1996 | Winterer et al. |
| 5,538,405 A | 7/1996 | Patno et al. |
| 5,540,568 A | 7/1996 | Rosen et al. |
| 5,547,453 A | 8/1996 | Di Perna |
| 5,551,850 A | 9/1996 | Williamson et al. |
| 5,551,941 A | 9/1996 | Howell |
| 5,551,942 A | 9/1996 | Brown et al. |
| 5,554,013 A | 9/1996 | Owens et al. |
| 5,570,716 A | 11/1996 | Kamen et al. |
| 5,578,070 A | 11/1996 | Utterberg |
| 5,609,572 A | 3/1997 | Lang |
| 5,614,677 A | 3/1997 | Wamsiedler et al. |
| 5,628,908 A | 5/1997 | Kamen et al. |
| 5,630,710 A | 5/1997 | Tune et al. |
| 5,634,896 A | 6/1997 | Bryant et al. |
| 5,640,995 A | 6/1997 | Packard et al. |
| 5,641,405 A | 6/1997 | Keshaviah et al. |
| 5,641,892 A | 6/1997 | Larkins et al. |
| 5,643,205 A | 7/1997 | Utterberg |
| 5,658,133 A | 8/1997 | Anderson et al. |
| 5,690,602 A | 11/1997 | Brown et al. |
| D390,654 S | 2/1998 | Alsberg et al. |
| 5,713,865 A | 2/1998 | Manning et al. |
| 5,713,888 A | 2/1998 | Neuenfeldt et al. |
| 5,741,125 A | 4/1998 | Neftel et al. |
| 5,746,708 A | 5/1998 | Giesler et al. |
| 5,755,683 A | 5/1998 | Houle et al. |
| 5,764,034 A | 6/1998 | Bowman et al. |
| 5,771,914 A | 6/1998 | Ling et al. |
| 5,772,635 A | 6/1998 | Dastur et al. |
| 5,772,637 A | 6/1998 | Heinzmann et al. |
| 5,782,805 A | 7/1998 | Meinzer et al. |
| 5,799,207 A | 8/1998 | Wang et al. |
| 5,816,779 A | 10/1998 | Lawless et al. |
| 5,840,151 A | 11/1998 | Munsch |
| 5,842,841 A | 12/1998 | Danby et al. |
| 5,843,035 A | 12/1998 | Bowman et al. |
| 5,868,696 A | 2/1999 | Giesler et al. |
| 5,873,853 A | 2/1999 | Keilman et al. |
| 5,906,598 A | 5/1999 | Giesler et al. |
| 5,921,951 A | 7/1999 | Morris |
| 5,925,011 A | 7/1999 | Faict et al. |
| 5,935,099 A | 8/1999 | Peterson et al. |
| 5,938,634 A | 8/1999 | Packard |
| 5,989,423 A | 11/1999 | Kamen |
| 5,993,174 A | 11/1999 | Konishi |
| 5,996,634 A | 12/1999 | Dennehey et al. |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,065,941 A | 5/2000 | Gray et al. |
| 6,068,612 A | 5/2000 | Bowman et al. |
| 6,074,359 A | 6/2000 | Keshaviah et al. |
| 6,099,492 A | 8/2000 | Le Boeuf |
| 6,110,410 A | 8/2000 | Owens et al. |
| 6,118,207 A | 9/2000 | Ormerod et al. |
| 6,129,517 A | 10/2000 | Danby et al. |
| 6,136,565 A | 10/2000 | Best et al. |
| 6,154,605 A | 11/2000 | Aonuma |
| 6,164,621 A | 12/2000 | Bouchard et al. |
| 6,165,154 A | 12/2000 | Gray et al. |
| 6,179,801 B1 | 1/2001 | Holmes et al. |
| 6,184,356 B1 | 2/2001 | Anderson et al. |
| 6,196,987 B1 | 3/2001 | Holmes et al. |

(56) References Cited

U.S. PATENT DOCUMENTS

| | | | |
|---|---|---|---|
| 6,200,287 B1 | 3/2001 | Keller et al. |
| 6,208,107 B1 | 3/2001 | Maske et al. |
| 6,220,295 B1 | 4/2001 | Bouchard et al. |
| 6,223,130 B1 | 4/2001 | Gray et al. |
| 6,227,807 B1 | 5/2001 | Chase |
| 6,228,047 B1 | 5/2001 | Dadson |
| 6,231,537 B1 | 5/2001 | Holmes et al. |
| 6,234,989 B1 | 5/2001 | Brierton et al. |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,315,707 B1 | 11/2001 | Smith et al. |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,382,923 B1 | 5/2002 | Gray |
| 6,383,158 B1 | 5/2002 | Utterberg |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,484,383 B1 | 11/2002 | Herklotz |
| 6,489,896 B1 | 12/2002 | Platt et al. |
| 6,491,656 B1 | 12/2002 | Morris |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,645,166 B2 | 11/2003 | Scheunert et al. |
| 6,645,177 B1 | 11/2003 | Shearn |
| 6,648,861 B2 | 11/2003 | Platt et al. |
| 6,663,359 B2 | 12/2003 | Gray |
| 6,670,323 B1 | 12/2003 | Looker et al. |
| 6,672,841 B1 | 1/2004 | Herklotz et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Dönig et al. |
| 6,746,514 B2 | 6/2004 | Bedingfield et al. |
| 6,749,403 B2 | 6/2004 | Bryant et al. |
| 6,752,172 B2 | 6/2004 | Lauer |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 * | 1/2005 | Kline et al. ..................... 417/46 |
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,969,373 B2 | 11/2005 | Schwartz et al. |
| 6,984,218 B2 | 1/2006 | Nayak et al. |
| 7,021,148 B2 | 4/2006 | Kuhn et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman, Jr. et al. |
| 7,195,607 B2 | 3/2007 | Westberg et al. |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 * | 7/2007 | Childers et al. ............... 604/6.11 |
| 7,255,680 B1 | 8/2007 | Gharib |
| 7,258,534 B2 | 8/2007 | Fathallah et al. |
| 7,267,661 B2 | 9/2007 | Susi |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,286 B2 | 2/2010 | Childers et al. |
| 7,699,966 B2 | 4/2010 | Qin et al. |
| 7,789,849 B2 | 9/2010 | Busby et al. |
| 7,815,595 B2 | 10/2010 | Busby et al. |
| 7,867,189 B2 * | 1/2011 | Childers et al. .................. 604/29 |
| 2001/0034502 A1 | 10/2001 | Moberg |
| 2001/0037763 A1 | 11/2001 | Deguchi et al. |
| 2002/0045851 A1 | 4/2002 | Suzuki et al. |
| 2002/0062105 A1 | 5/2002 | Tanner et al. |
| 2002/0062109 A1 | 5/2002 | Lauer |
| 2002/0072718 A1 | 6/2002 | Brugger et al. |
| 2002/0107474 A1 | 8/2002 | Noack |
| 2002/0147423 A1 | 10/2002 | Burbank et al. |
| 2003/0018395 A1 | 1/2003 | Crnkovich et al. |

(56) References Cited

U.S. PATENT DOCUMENTS

| | | |
|---|---|---|
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220627 A1 | 11/2003 | Distler et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1* | 2/2004 | Suzuki et al. ............. 210/646 |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0135078 A1 | 7/2004 | Mandro et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0165354 A1 | 7/2005 | Schwartz et al. |
| 2005/0209563 A1 | 9/2005 | Hopping et al. |
| 2005/0230292 A1 | 10/2005 | Beden et al. |
| 2006/0079826 A1 | 4/2006 | Beden et al. |
| 2006/0145105 A1* | 7/2006 | Ishida et al. ............. 251/7 |
| 2006/0195064 A1 | 8/2006 | Plahey et al. |
| 2007/0112297 A1 | 5/2007 | Plahey et al. |
| 2007/0149913 A1* | 6/2007 | Busby et al. ............. 604/5.04 |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2008/0033346 A1 | 2/2008 | Childers et al. |
| 2008/0077068 A1 | 3/2008 | Orr |
| 2008/0208103 A1 | 8/2008 | Demers et al. |
| 2009/0004033 A1 | 1/2009 | Demers et al. |
| 2011/0040242 A1 | 2/2011 | Fallon et al. |

FOREIGN PATENT DOCUMENTS

| | | |
|---|---|---|
| DE | 100 42 324 | 2/2002 |
| DE | 100 46 651 | 4/2002 |
| DE | 19919572 C2 | 4/2002 |
| DE | 100 53 441 | 5/2002 |
| DE | 101 57 924 | 5/2002 |
| DE | 101 43 137 | 4/2003 |
| EP | 0410125 B1 | 8/1993 |
| EP | 0728509 | 8/1996 |
| EP | 0 947 814 B2 | 10/1999 |
| EP | 0 956 876 A1 | 11/1999 |
| EP | 1529545 | 5/2005 |
| JP | 0396850 A | 4/1991 |
| JP | 04-191755 | 7/1992 |
| JP | 06-154314 | 6/1994 |
| JP | 06-002650 | 11/1994 |
| JP | 11-347115 | 12/1999 |
| JP | 2000-070358 | 3/2000 |
| WO | WO 84/02473 | 7/1984 |
| WO | WO 86/01115 | 2/1986 |
| WO | WO 97/16214 | 5/1997 |
| WO | WO 97/37703 | 10/1997 |
| WO | WO 98/22165 | 5/1998 |
| WO | WO 00/23140 | 4/2000 |
| WO | WO 00/33898 | 6/2000 |
| WO | WO 01/17605 | 3/2001 |
| WO | WO 02/25225 | 3/2002 |

OTHER PUBLICATIONS

International Preliminary Report on Patentability in PCT/US2006/003921 dated Nov. 22, 2007 (6pp.).

International Search Report and Written Opinion of the International Searching Authority in PCT/US2007/077119 dated Apr. 29, 2008 (16pp.).

International Search Report and Written Opinion of the International Searching Authority in PCT/US2007/077119 dated Jun. 11, 2008 (7pp.).

International Search Report and Written Opinion of the International Searching Authority in PCT/US2007/077119 dated Nov. 6, 2008 (10pp.).

International Search Report and Written Opinion of the International Searching Authority in PCT/US2006/003921 dated Sep. 24, 2007 (10pp.).

Sleep Safe Operating Instructions, Software Version 0.9, Part No. 677 805 1, Fresenius Medical Care, Aug. 2000.

Gambro®, Prisma® HF 1000, "For Increased Filtration Capacity", © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Liberty Cycler User's Guide ©, 2008, pp. 1-174.

Manns, Markus et al., "The acu-men: A new device for continuous renal replacement therapy in acute renal failure," Kidney International, vol. 54, pp. 268-274, 1998.

Newton IQ Cycler Operator Manual, Part No. 470203 Rev. F, 2000-2006.

Operator's Instructions, Fresenius 90/2 Peritoneal Therapy Cycler, Part No. 470016 Rev. B, 1991.

Operator's Manual, Serena, Program Version 3.xx—English.

Sleep Safe Technical Manual, Part No. 677 807 1.

Glenn Avolio, "Principles of Rotary Optical Encoders," Sensors Journal of Machine Perception, vol. 10, No. 4, pp. 10-18, 1993.

Bolegoh, Gordon, "Pumps: Reference Guide", p. 24, 3rd edition, 2001.

Ronco et al, "Evolution of Machines for Automated Peritoneal Dialysis", in Automated Peritoneal Dialysis, Contributions to Nephrology, vol. 129, pp. 142-161, 1999.

Sleep Safe Operating Instructions, Software Version 0.5, Apr. 1999.

Sleep Safe Operating Instructions, Software Version 1.0, Oct. 2000.

Sleep Safe Technical Manual, Dec. 2001.

Sleep Safe Operating Instructions, Jan. 2002.

Sleep Safe Communicating Therapy, Mar. 1998.

Sleep Safe Kommunizierte Therapie, May 1998.

Innovative Technologies in Peritoneal Dialysis, Sleep Safe Concept, Oct. 13, 1999 (4 attachments).

Gambro®, "Prismaflex™ Anticipating Critical Care needs and taking our innovative response... to new heights," © 2004, Gambro Inc., Lakewood, CO, 8 pp.

Gambro®, "DEHP-Free Cartridge Blood Sets," © Nov. 2004, Gambro, Inc., Lakewood, CO, 4 pp.

Acumen, "Acute Dialysis Machine Brief Operating Instructions," Software Version 1.0, pp. 1-146, May 1996.

Operator's Manual, Serena, Program Version 3.xx—English, 2002.

Sleep Safe Technical Manual, Part No. 677 807 1, Aug. 2000.

* cited by examiner

CASSETTE SYSTEM FOR PERITONEAL DIALYSIS MACHINE

CROSS-REFERENCE TO RELATED APPLICATIONS

This application is a continuation application of and claims priority to U.S. application Ser. No. 11/515,359, filed on Aug. 31, 2006, entitled "Improved Cassette System for Peritoneal Dialysis Machine," which is a continuation-in-part application of and claims priority to U.S. application Ser. No. 11/069,195, filed on Feb. 28, 2005, entitled "Portable Apparatus for Peritoneal Dialysis Therapy," each of which is incorporated by reference herein in its entirety.

BACKGROUND OF THE INVENTION

The present invention relates generally to apparatus for the treatment of end stage renal disease. More specifically, the present invention relates to portable apparatus for the performance of peritoneal dialysis.

Dialysis to support a patient whose renal function has decreased to the point where the kidneys no longer sufficiently function is well known. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because the treatment is extracorporeal, it requires special machinery and a visit to a center, such as in a hospital, that performs the treatment.

To overcome this disadvantage associated with hemodialysis, peritoneal dialysis (hereafter "PD") was developed. PD utilizes the patient's own peritoneum (a membranous lining of the abdominal body cavity) as a semi-permeable membrane. With its good perfusion, the peritoneum is capable of acting as a natural semi-permeable membrane.

PD periodically infuses sterile aqueous solution into the peritoneal cavity. This aqueous solution is called PD solution, or dialysate for short. Diffusion and osmosis exchanges take place between the solution and the blood stream across the peritoneum. These exchanges remove the waste products that the kidneys normally excrete. The waste products typically consist of solutes like urea and creatinine. The kidneys also function to maintain the proper levels of other substances, such as sodium and water, which also need to be regulated by dialysis. The diffusion of water and solutes across the peritoneal membrane during dialysis is called ultrafiltration.

In continuous ambulatory PD, a dialysis solution is introduced into the peritoneal cavity utilizing a catheter, normally placed into position by a visit to a doctor. An exchange of solutes between the dialysate and the blood is achieved by diffusion.

In many prior art PD machines, removal of fluids is achieved by providing a suitable osmotic gradient from the blood to the dialysate to permit water outflow from the blood. This allows a proper acid-base, electrolyte and fluid balance to be achieved in the body. The dialysis solution is simply drained from the body cavity through the catheter. The rate of fluid removal is dictated by height differential between patient and machine.

A preferred PD machine is one that is automated. These machines are called cyclers, designed to automatically infuse, dwell, and drain PD solution to and from the patient's peritoneal cavity. A cycler is particularly attractive to a PD patient because it can be used at night while the patient is asleep. This frees the patient from the day-to-day demands of continuous ambulatory PD during his/her waking and working hours.

The treatment typically lasts for several hours. It often begins with an initial drain cycle to empty the peritoneal cavity of spent dialysate. The sequence then proceeds through a succession of fill, dwell, and drain phases that follow one after the other. Each phase is called a cycle.

Unlike hemodialysis machines, which are operated by doctors or trained technicians, PD cyclers may be operated by the patient. Furthermore, many PD patients travel, which means taking their PD cyclers with them. Thus the insertion and operation of the cassette interface should be as ergonomic, safe and foolproof as possible, while exhibiting enhanced performance. The all-important design of the cassette itself should permit the maximum flexibility in functionality.

The intent of this invention is to provide improved PD equipment with a focus on the design of the cassette and cassette compartment of the PD cycler.

SUMMARY OF THE INVENTION

In one aspect the invention includes apparatus peritoneal dialysis apparatus including a disposable cassette compartment defined by a deck lying in a plane inclined from the vertical by about 10 to about 35 degrees, preferably about 20 to about 25 degrees, and more preferably about 22 degrees, having openings for valve actuators and piston heads and a door hinged from the side so as to close in parallel over the deck and enclose the cassette within the compartment. In one embodiment, the cassette has inlet/outlet connections along the bottom of the cassette, the compartment accommodating the connection of vertically hanging tubes to the inlet/outlet connections on the cassette so that preferably all of the inlet/outlet connections are in a line along the bottom edge of the cassette. In this configuration the lines are permitted to make a gentle bend substantially greater than 90 degrees when sitting on a flat surface.

In another aspect of the invention, a disposable PD solution routing cassette compartment is defined by a door and a cassette deck, and an inflatable pad carried by the door forces a cassette that fits into the compartment into sealing engagement with the cassette deck when the door is closed and the pad is inflated. In addition a door latch mechanism can be locked merely by the force of the inflatable pad tending to push the door away from the cassette deck.

In another aspect of the invention a disposable PD solution cassette defining channels, valves and pump chambers for routing PD solution to and from inlet/outlet connections on the cassette is arranged in a cassette compartment with a cassette deck for sealingly engaging the cassette, the cassette having a diaphragm covering at least one pump chamber facing the deck, the deck having a reciprocating piston head mounted for reciprocation in a cylindrical chamber, an annular space surrounding the piston head between the chamber walls, and a pneumatic system draws a vacuum in the cylindrical chamber, the vacuum drawing the diaphragm tight against the piston head so that the diaphragm retracts with the piston head. The pneumatic system can also be used to seal a pressure reading area of the cassette to a pressure sensor on the deck.

A further aspect of the invention is the design of a disposable cassette for routing PD solution with a molded plastic panel having a circumferential fluid channel defined along the perimeter of the panel.

Finally, another aspect of the invention involves a method of operating a PD machine, for example, using a cassette system with some of the features disclosed herein, to drain spent PD solution from the patient to an empty solution bag that had been filled with PD solution earlier that was used to infuse the same patient to take a sample of the used PD solution.

The details of one or more embodiments of the invention are set forth in the accompanying drawings and the description below. Other features, objects, and advantages of the invention will be apparent from the description and drawings, and from the claims.

DESCRIPTION OF DRAWINGS

Numbers referring to the same items in several drawings will bear the same reference numbers.

DETAILED DESCRIPTION OF THE PREFERRED EMBODIMENT

The Door Sealing Mechanism

Figure 1:
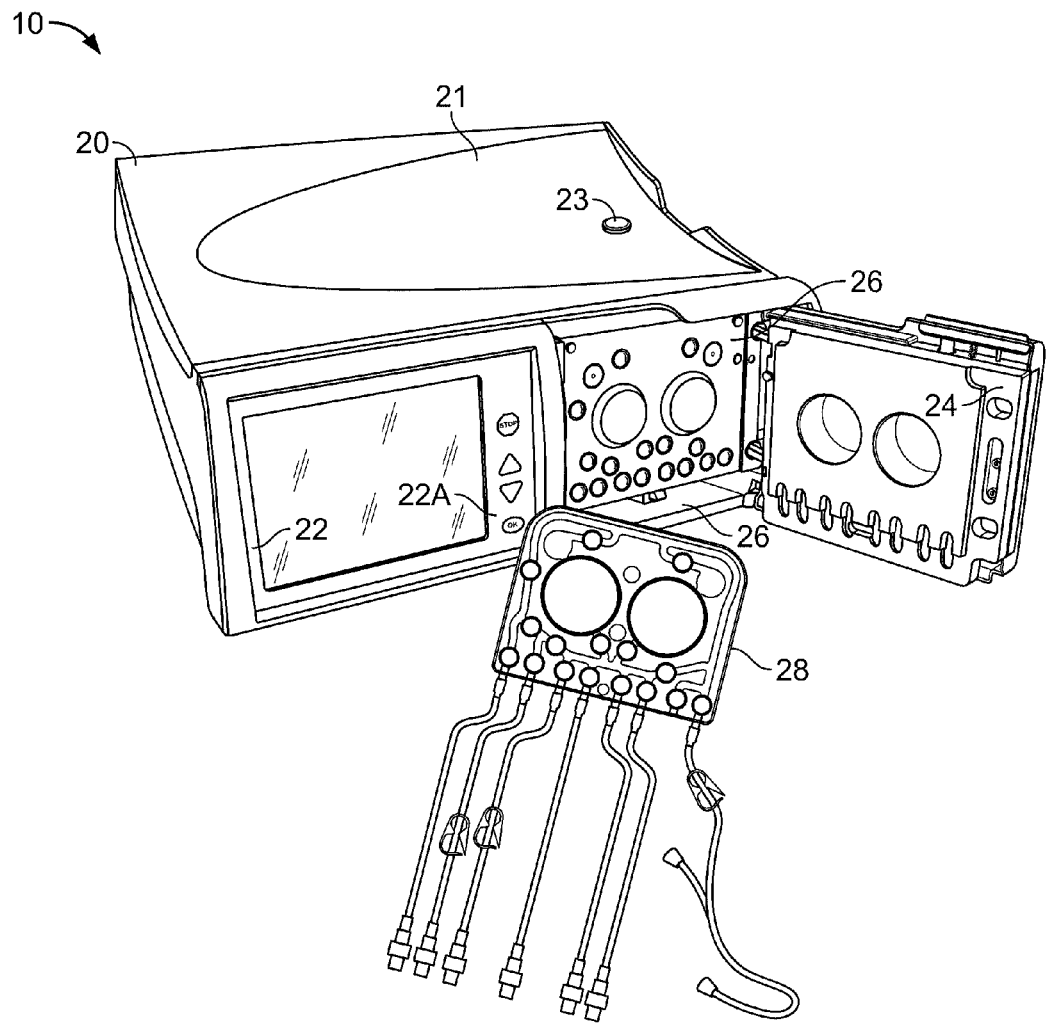
FIG. 1 is a perspective view of a PD cycler.

Referring to FIG. 1, the portable PD apparatus of the invention is shown in an embodiment of a PD cycler 10. The housing 20 holds a touch screen 22, along with additional control buttons 22A forming the control panel for the user interface operated by the patient. A cassette holder includes a hinged door 24 and a cassette support deck 26. The cassette 28, shown in FIG. 4, fits into the cassette support deck 26. A cassette is inserted into the support deck 26 and the door 24 is closed on the cassette and securely latched, as will be described later.

Figure 2:
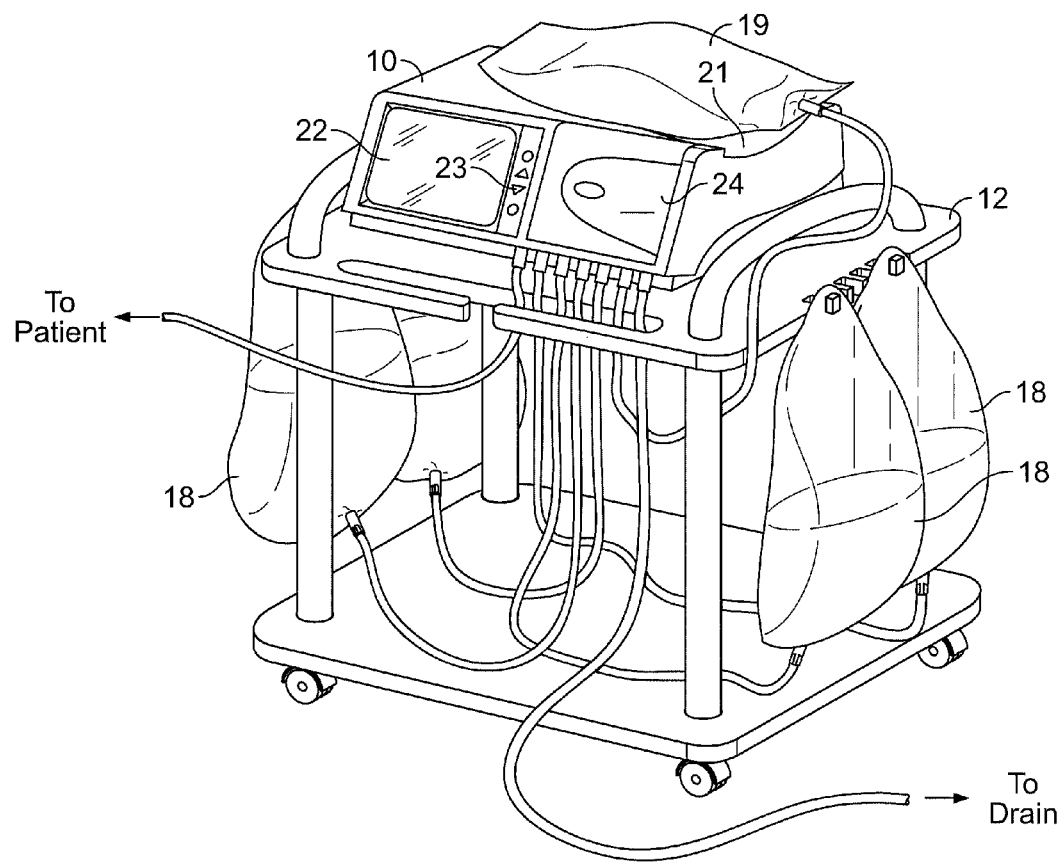
FIG. 2 is a perspective view of the PD cycler of FIG. 1 on a special cart with a heater bag on the heater tray and additional PD solution bags for more exchanges hanging off the cart.

FIG. 2 shows the PD cycler 10 with some of its accessories to illustrate how it used. The cycler 10 is seated on top of a cart 12 designed to accommodate the PD solution bags and associated tubing. The disposable cassette 28 (FIG. 1) locked inside door 24 includes channels, flexible valve domes and diaphragm covered pumping chambers described below that are actuated by mating pneumatic valves and pistons interfacing with the cassette compartment to route the flow of PD solution from the bags through the cycler to the patient and from the patient to a drain. The cassette itself has tubing connectors 16 arrayed along its bottom edge. The connectors extend beneath the door 24 and are connected to tubing as shown in FIG. 2.

Figure 3:
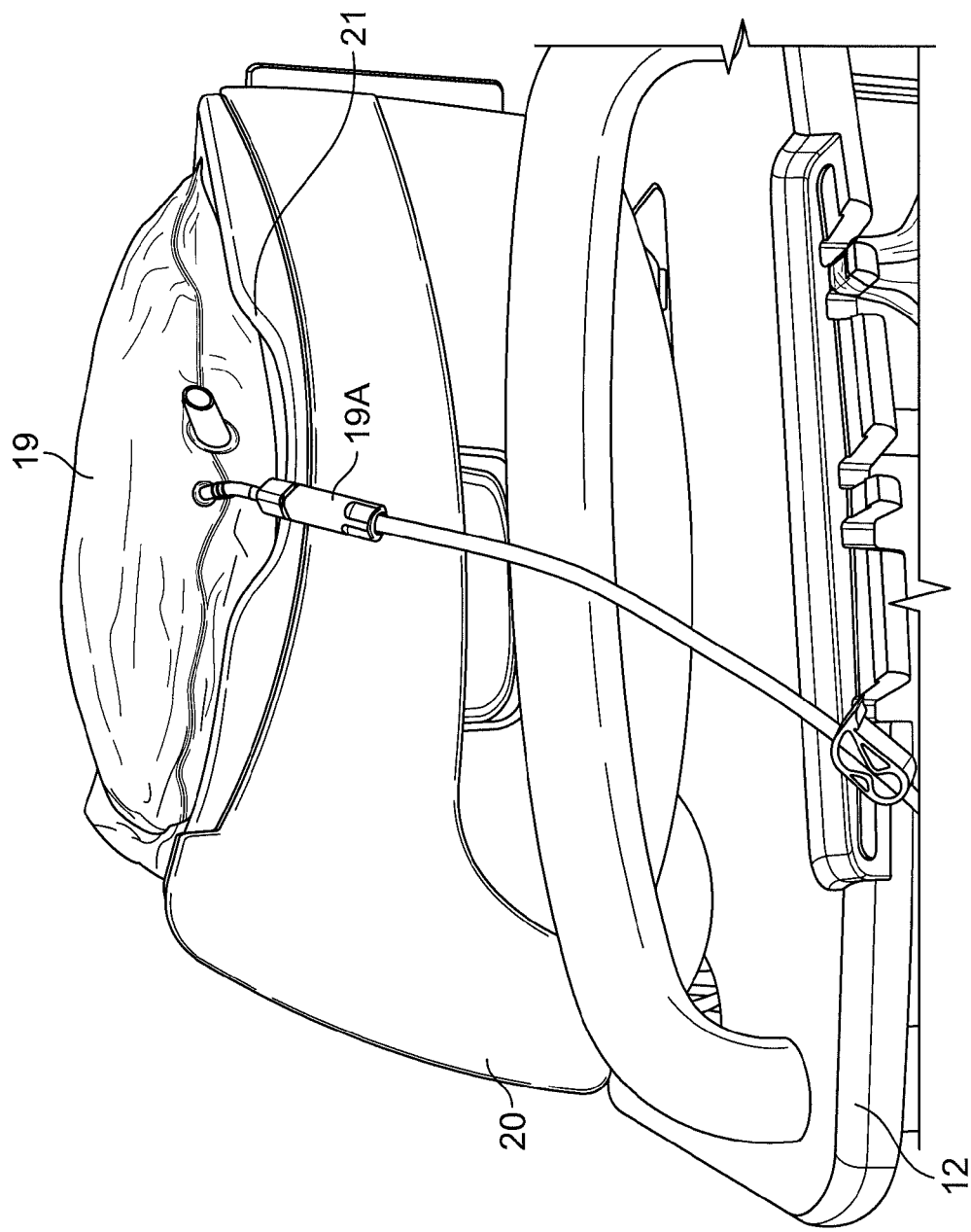
FIG. 3 is an end view of the PD cycler of FIGS. 1 and 2 showing the angle of the front and the heater bag outlet.

PD solution bags 18 are suspended from fingers on the sides of the cart 12 as shown. A heater bag 19 is shown lying in a shallow concave depression forming the heater tray 21, which is sized and shaped to accommodate a typical 5 L bag of PD solution. The heater tray 21 has a plurality of heating coils (not shown) embedded below the surface. The surface of the tray 21, as better shown in FIGS. 1 and 3, is slightly inclined downward to the right to assist in emptying the heater bag which is arranged so that the outlet 19A of the heater bag is also at the right side, adjacent to a temperature sensor 23 positioned in the surface of the heater tray 21 to track the temperature of the solution in the heater bag for a thermostatic control circuit that turns the heating coils on and off as needed to maintain the PD solution at the desired temperature. A dual voltage heating system for the heater tray 21 is disclosed in accompanying application Ser. No. 11/513,618, filed the same day as this application, by Kulwinder Plahey, assigned to the same assignee, entitled "Peritoneal Dialysis Machine with Dual Voltage Heater Circuit and Method of Operation," which is incorporated by reference herein in its entirety. The dual voltage heating system automatically reconfigures the heating circuit depending on detection of either 110 VAC or 220 VAC to deliver the same wattage for heating PD solution before delivery to the patient, thus facilitating use of the same machine in the United States and Europe.

Figure 4:
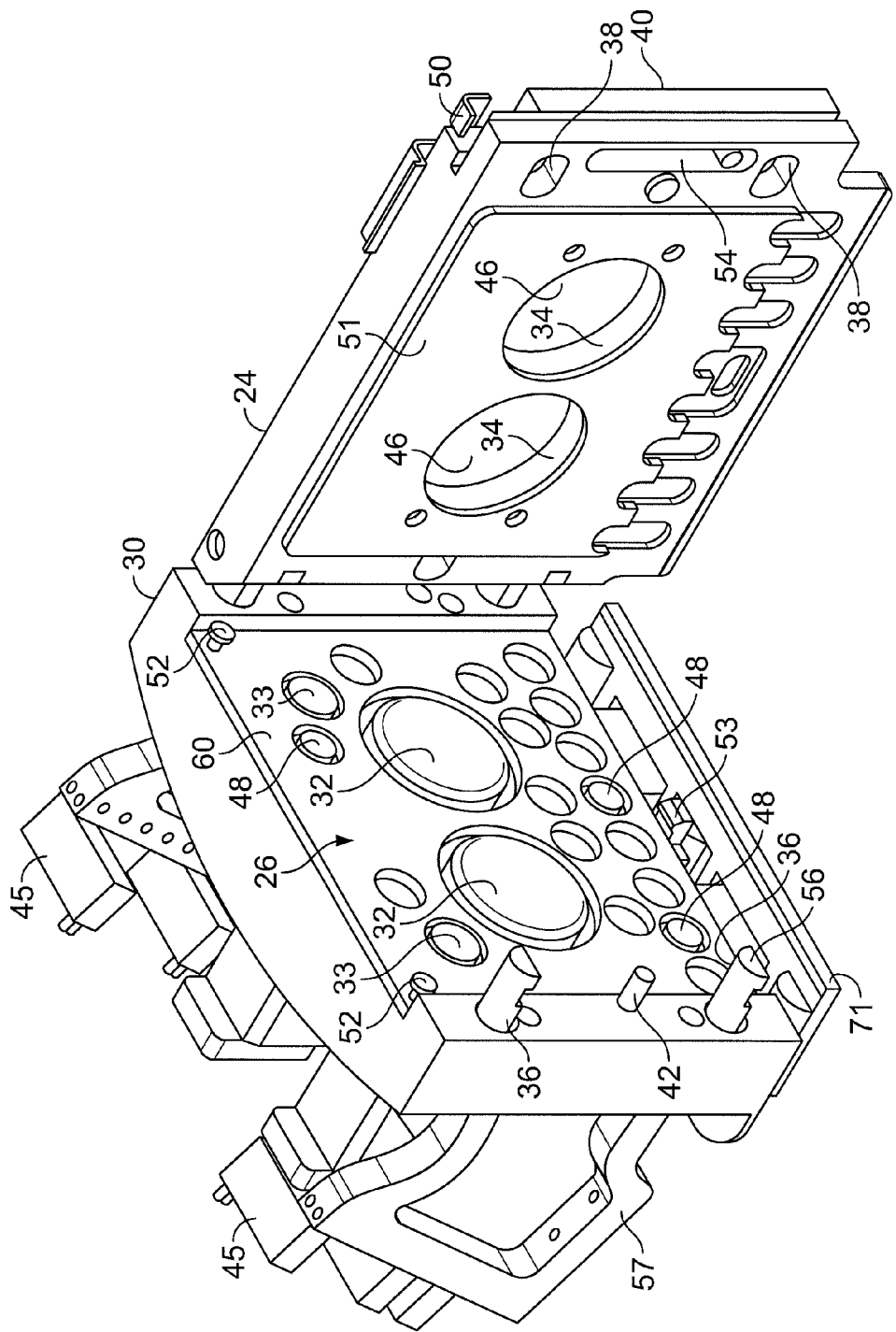
FIG. 4 is a perspective view of the cassette holder of the PD cycler of FIG. 1.

The heater tray 21 is also mounted internally on a support equipped with a load cell (not shown) to provide an electrical signal indicating the weight of the contents of the PD solution bag to tell the cycler control system how full the heater bag is with PD solution. Referring to FIGS. 4, 5, 6, 7A, 7B, 8, 9, 10A and 10B, the cassette compartment 60 will now be described in detail. Essentially, the cassette compartment 60 consists of a base 30 and door 24 hinged to the base 30 on the right side, as shown in FIG. 4. Base 30 incorporates two pumps 44 having exposed mushroom heads 32. Mating with these heads are two cylindrical chambers 34 that accommodate the rigid domes for the pump chambers on the cassette 28 within door 24. The base 30 also includes a pair of door latches 36 that mate with holes 38 in door 24. The door also has a sliding latch 40 or catch slide. Microswitch 42 provides an electrical indication of whether the door is opened or fully closed.

It is necessary that a very tight, secure mechanical enclosure be provided with intimate contact with the cassette 28 (FIG. 4) when the machine is in operation. Prior art PD machines provided this tight enclosure by using a tight door latch that had to be almost forced closed by the patient. This created a problem for elderly or very ill patients who lacked the strength to close the door. Alternatively, in other prior art PD machines, cassettes were inserted using a complicated mechanism, similar to a VCR, making servicing more difficult. Accordingly, the PD apparatus of this invention does not require the patient to close the door with sufficient force to make all the necessary seals. Furthermore, the cassette can be set directly into compartment 60 without use of the more complicated, VCR-like apparatus.

Figure 7A:
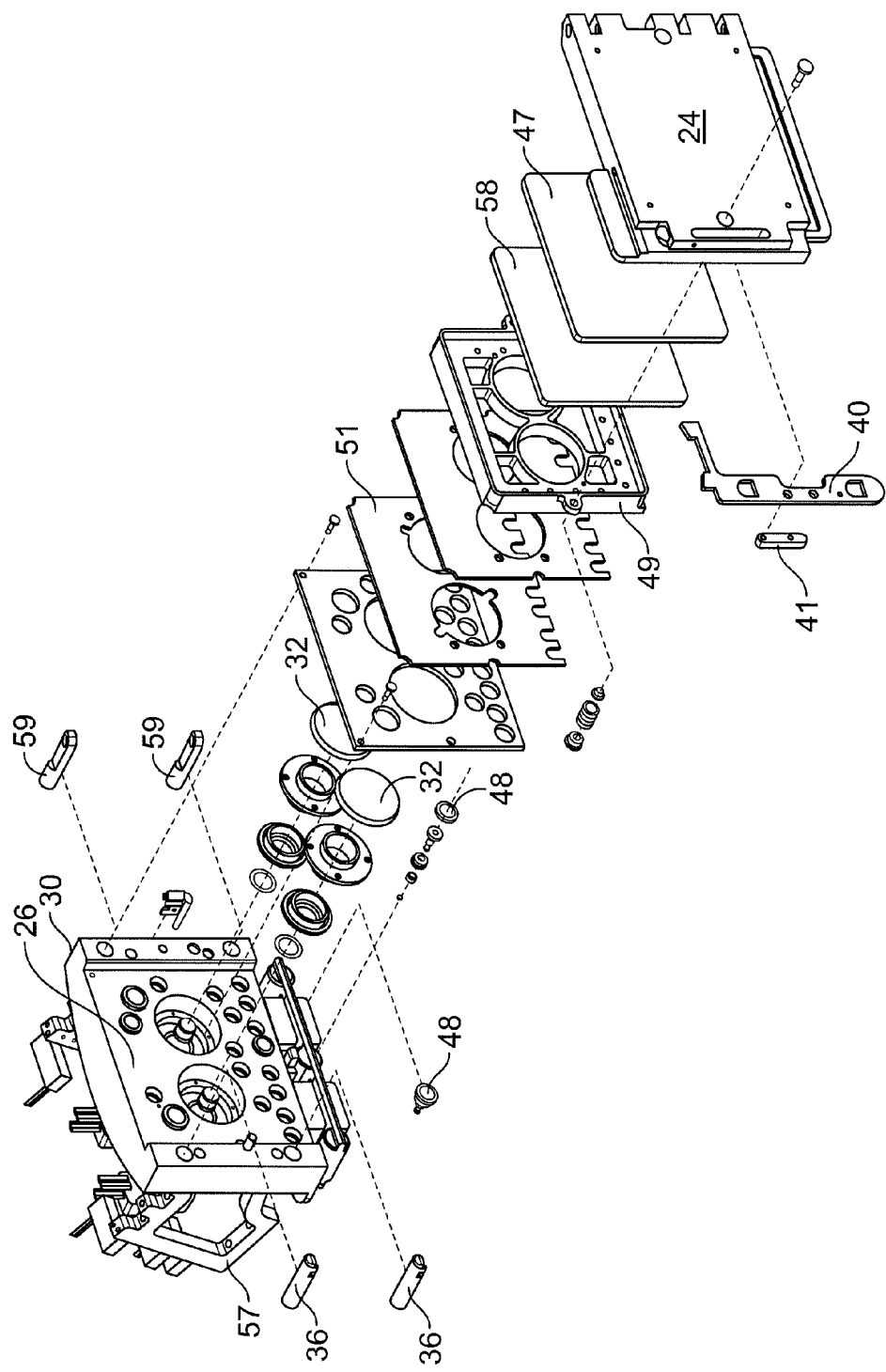
FIGS. 7A and 7B are exploded perspective views of the cassette holder of FIG. 4, FIG. 7A showing the front of the cassette deck and door assembly, and FIG. B showing the back of the cassette deck and internal components behind the cassette deck, as well as the safety clamp

Door 24 is lightly latched using latch lever 40 and latch posts 36, which loosely engage with holes 38. Although the door easily "clicks" shut, the proper seals are not made by this closing. To insure that the cassette 28 is in intimate and sealed contact with both the base 30 and the door 24, the PD apparatus of the invention uses an inflatable pad 47, shown in FIG. 7A. In front of the pad 47 is a displaceable spacer 49 mounted to the pad 47 by means of a plate 58. One or more molded plastic pressure pads 51 are bonded to the front of the spacer 49 for engaging the cassette. The cassette is held in place between the cassette pad 51 and the cassette deck 26, as shown in FIGS. 4 and 7A. Once the door is lightly shut and latched by the patient, and the system receives a signal to that effect from microswitch 42, pressurized air is pumped into pad 47, squeezing the cassette between the door 24 and the cassette deck 26, as shown in FIG. 4. The pressure applied should be adequate so that all necessary seals are made. Thus even though the cassette will wind up being under pressure, the patient does not need to exert any force on the door or latch to close the door.

To open door 24 to load a cassette, button 50 on the top left edge of the door (FIG. 4) is depressed. This will disengage the door lock. The door then swings open from left to right. Cassette 28 (FIG. 11) may then be loaded into cassette holder by putting the top of the cassette under the locating pins 52. The bottom edge of the cassette will be snapped in place over a spring loaded center clip 53 (FIG. 4). The door 24 closes from right to left pushing gently on it to automatically engage the door with latch posts 36. The catch assembly is comprised of a catch slide 40 a mounting slide block 41 to which it is attached (FIG. 7A) and a catch tension spring (not shown). The block slides in a machined slot 54 on the left side of the door as viewed in a closed position (FIG. 4). As the door swings shut, the catch slide comes in contact with the beveled end 56 of the latch posts 36. The action of lightly pushing on the door to latch it also actuates the door safety switch 42. The catch slide lowers and then springs upward in the notches formed by the latch posts 36, coming to rest with the flat blade of the catch slide in contact with the forward planar wall of the notches in the latch posts. When the door is not pressurized the friction between the contact area of the latch post notch walls and the catch slide blade is easily overcome to re-open the door. However, when the compartment is pressurized by the inflatable pad 47, the friction between these elements cannot be overcome by the user who will be unable to push the catch slide 40 downward with enough force to overcome the contact friction with the post notch walls. Thus the pressurization of the door acts as a safety interlock for the cassette compartment.

Once the door safety switch is closed, the system receives an electrical signal indicating that it is ready to clamp the cassette into the cassette holder by inflating the cassette clamping inflatable pad 47 ((FIG. 3A) with approximately 37 psi pressure (which generates approximately 1000 pounds of force). This clamps the cassette 28 against the clamp pad 51 (FIG. 3A), thereby rigidly holding the cassette in place so that it can be operated by the valves and pistons in the cassette deck. The door locking mechanism is then immobilized, preventing the door from accidentally opening or even from being opened by the patient, for safety purposes.

Figure 10A:
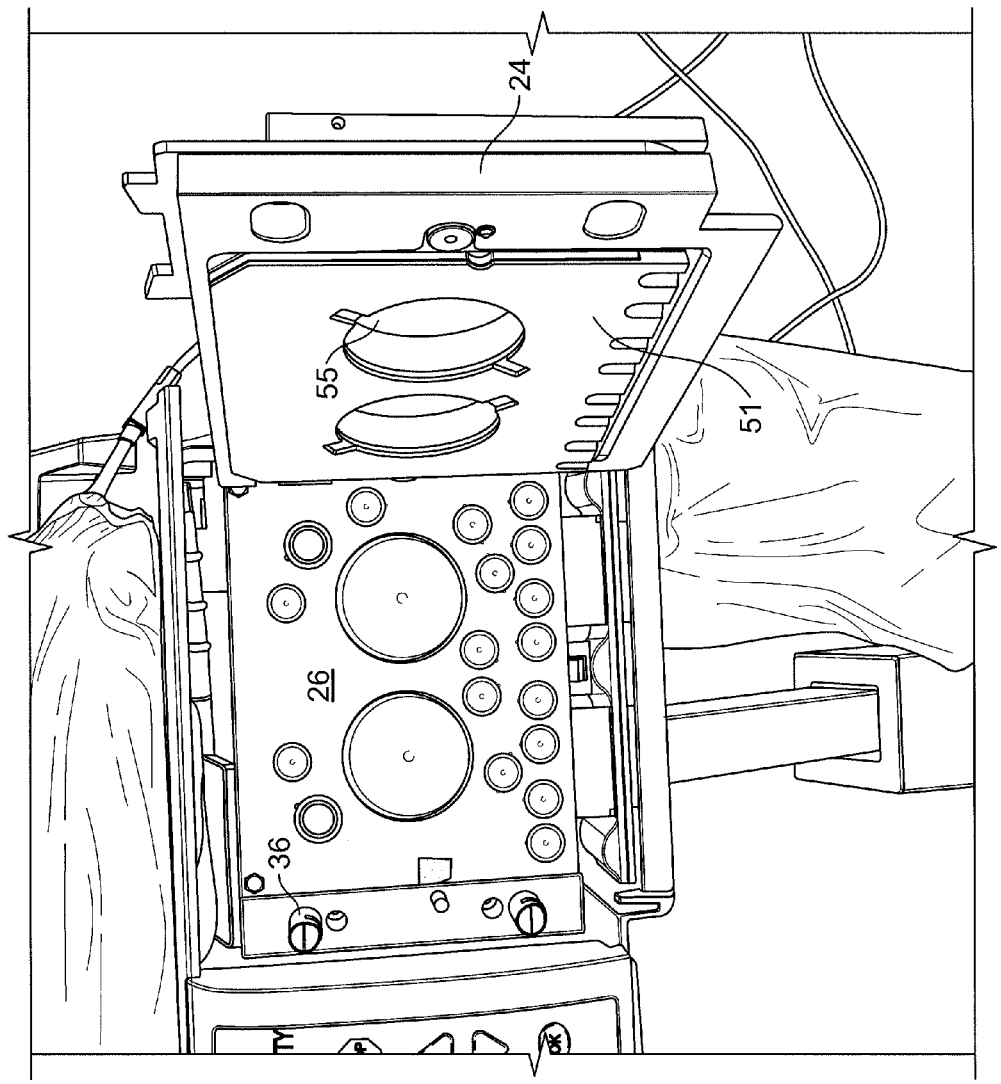
FIGS. 10A and 10B are perspective views of the cassette holder of the PD cycler of FIG. 2 showing the displacement of the door cassette pad when pressurized from the retracted uninflated position in FIG. 10A to the fully inflated, extended position in 10B, which of course only happens when the door is closed with the cassette in place.
Figure 10B:
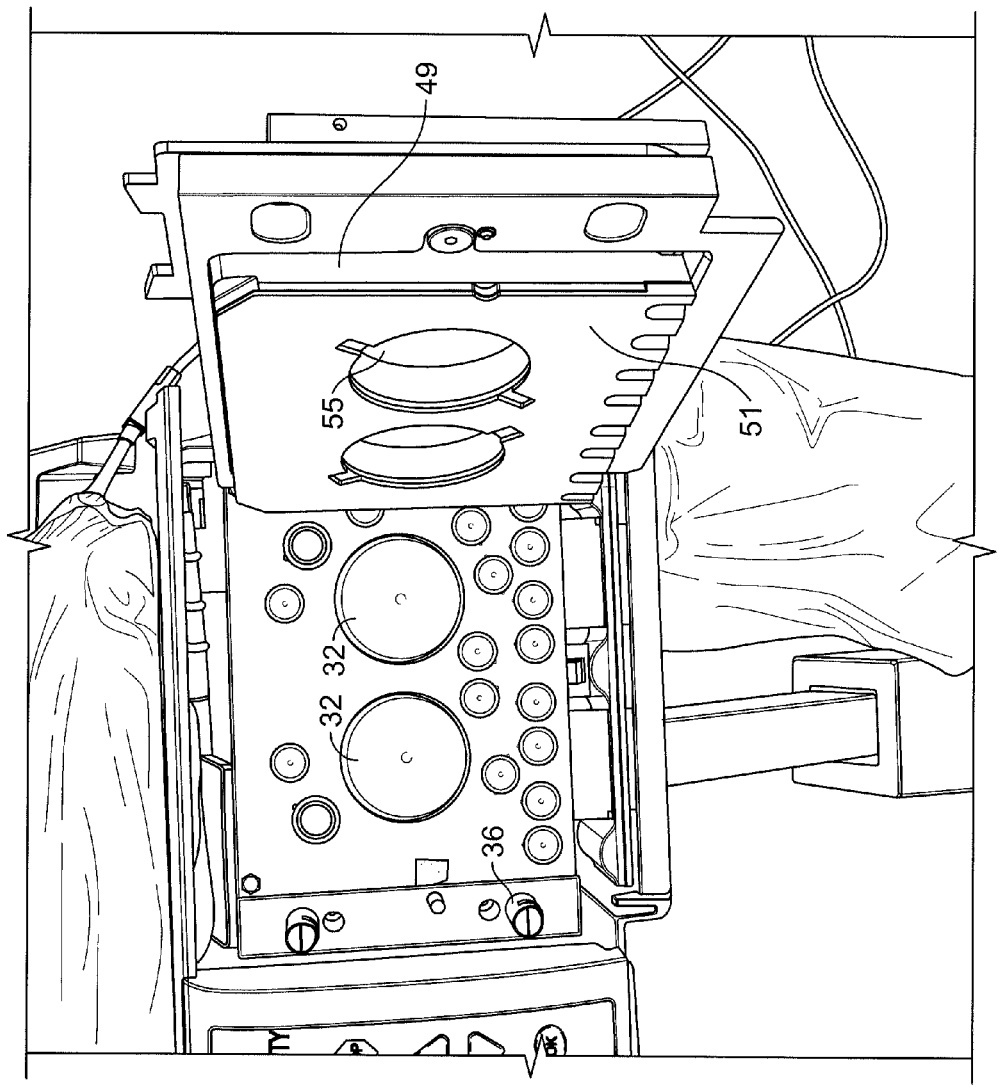
Figure 11:
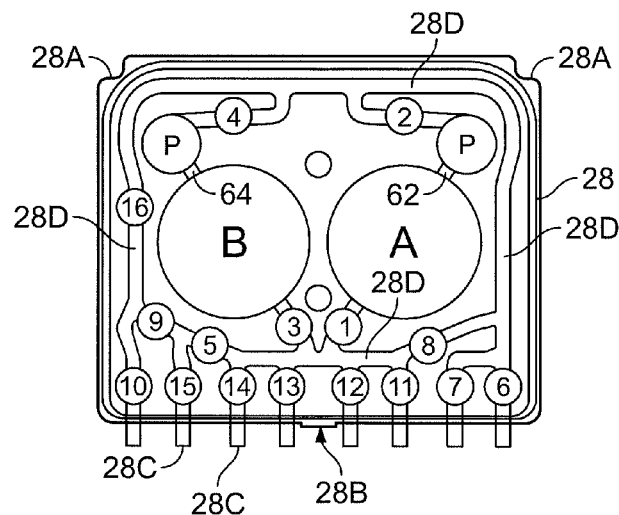
FIG. 11 is a view of a cassette used in the apparatus of the invention, the view being of the side that faces the cassette deck, i.e., the machine, when inserted.

There are several ergonomic features of the basic arrangement of the cassette compartment 60 and door 24. As shown in the end views in FIGS. 5 and 6, the brackets 57 that hold the base 30 of the cassette deck and also support the hinges 59 for the door, are designed to hold the base and door at a 10 to 35 degree angle to the vertical, preferably 22 degrees. Thus the hinge line of the door itself is inclined rather than plumb and the deck 36 where the cassette is mounted is also in a reclining orientation. When the user opens the door as shown in FIGS. 1 and 10A, for example, the door tends to hold itself open when opened past 90 degrees because of this inclination. In addition, the surface of the deck where the cassette is to be mounted is more easily viewed and accessed by the user because of the angle, particularly because the compartment would rarely be at eye level. The user must assure that the cassette is inserted correctly with the notches 28A (FIG. 11) under the pins 52 (FIG. 4) and the lower center edge of the cassette 28B snapped in place over the clip 53. (Note that the side of the cassette 28 in view in FIG. 11 is the one that fits against the cassette deck, so when in place, the cassette 28 will appear reversed.) This is more easily accomplished with the compartment at this approximate angle.

A further advantage of the cassette compartment design is achieved by virtue of the door being hinged from the side. With this arrangement, the cassette is free to have the tubing connections (inlets and outlets), of which there are typically seven in use, arrayed along the bottom edge of the cassette as shown in FIGS. 1 and 11 with the tubing hanging straight down. This permits the tubes to hang free and untangled, straight down under the force of gravity if there is a slot on the table as shown in FIG. 2 without any unnecessary bending likely to kink or constrict the lines. In combination with this bottom entry feature, the 22 degree angle of the door compartment better accommodates a bend in the lines if the cycler is sitting on a night table for example where the lines would extend downward and then across the table top for a few inches. If the compartment was vertical the lines would have to make a 90 degree turn. Instead they can take a gentler 112 degree turn on the table top or other flat surface and remain free of constriction.

The Pump

Figure 5:
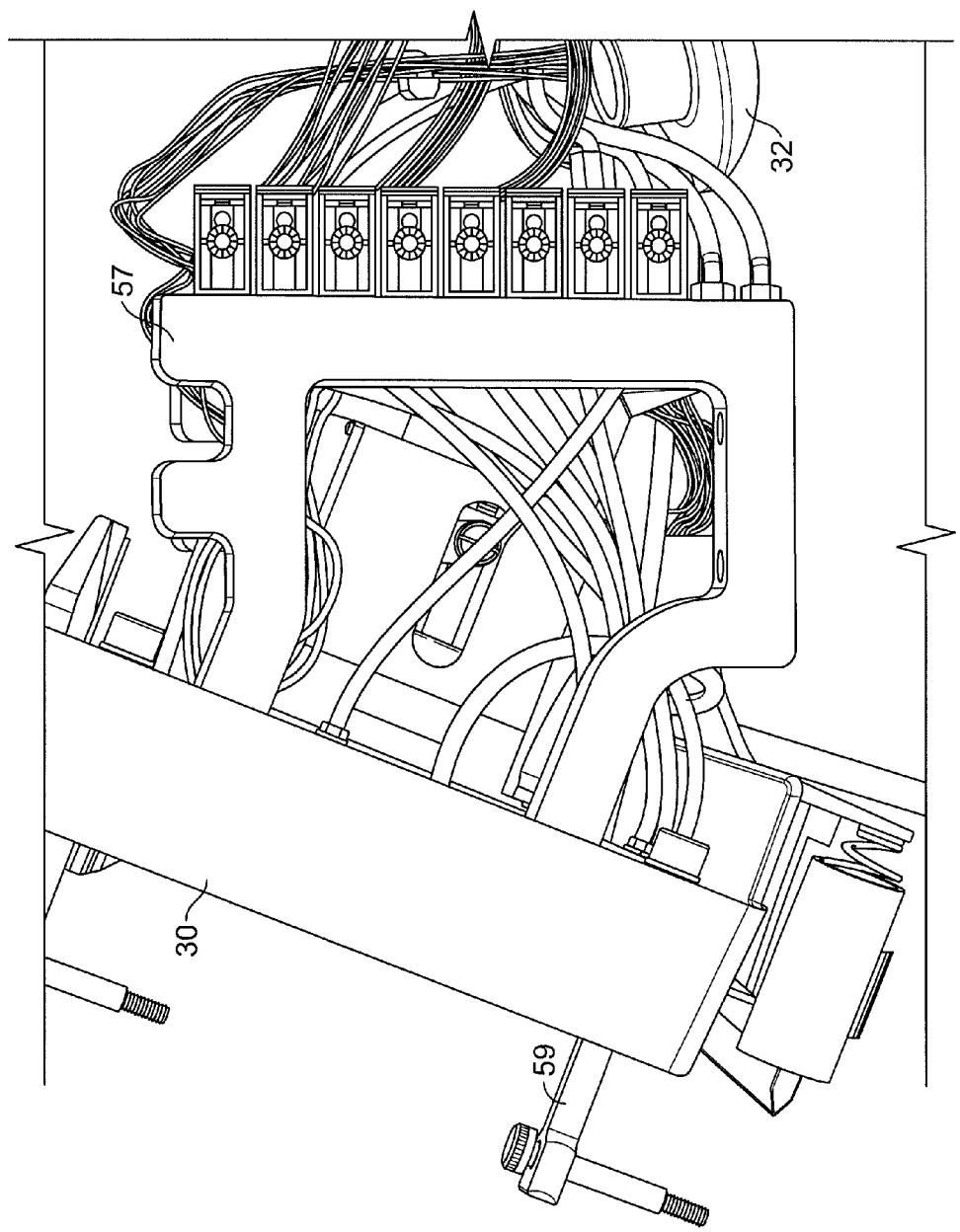
FIGS. 5 and 6 are end views of the bracket and cassette deck of an embodiment of the cassette holder of FIG. 4 showing the angle of the cassette deck.
Figure 9:
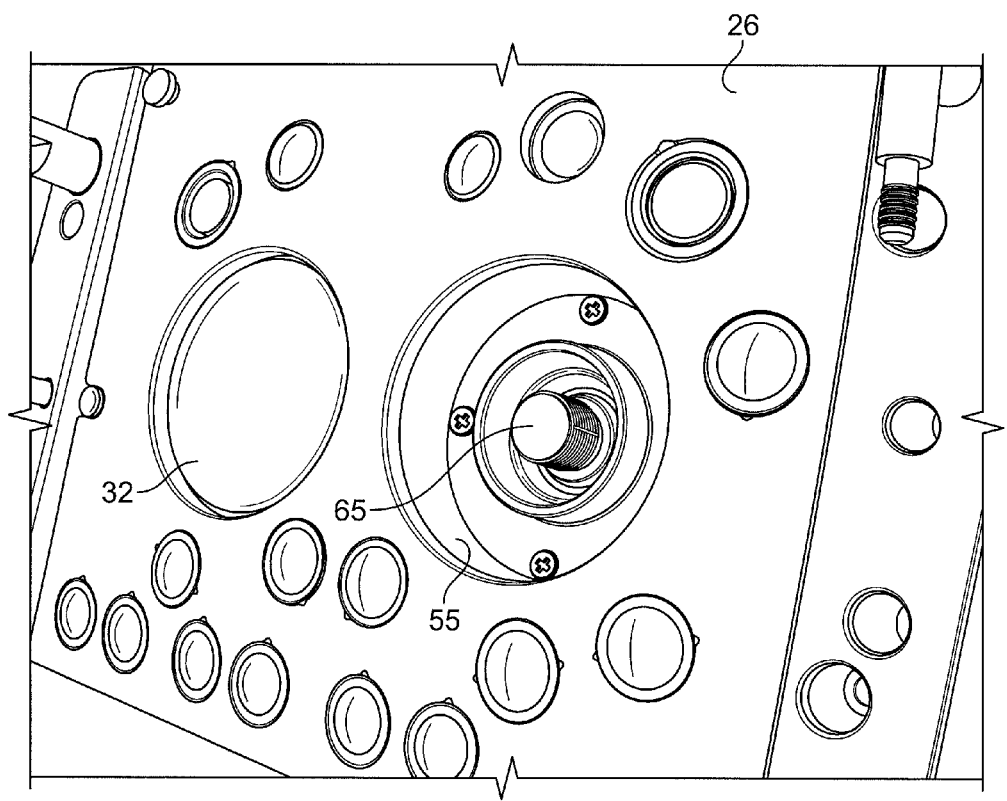
FIG. 9 is a detail perspective view of the front of the cassette deck of FIG. 8 with one of the mushroom piston heads removed.

The pumps 44 (best seen in FIG. 7B) are controlled by stepper motors 45. The details of the stepper motor control will be explained later. The PD apparatus of the invention uses two modes of pumping, simultaneous and alternating. With the alternating method, while one pump is protracted, the other is retracted. Simultaneous pumping is where both pump heads extend at the same time in the same direction, and both retract at the same time. Each pump has a piston with a mushroom shaped head 32 as shown in FIGS. 4 and 5. The mushroom head 32 has a threaded bore which screws onto a threaded post 65 on the piston shaft as shown in FIG. 5. The outer diameter of the head 32 is slightly less than the inner diameter of the cylinder 55 in which the head reciprocates as shown in FIG. 9. The inner wall of each cylinder has a slot (not shown) in the form of a circumferential arc in the wall to allow evacuation of air from the piston chamber, as described below.

To move fluid out of one of the pump chambers, the mushroom head 32 mated to that chamber is protracted all the way to the rigid back dome of the cassette 28, but not touching it. To draw fluid into one of the pump chambers, the piston head 32 is pulled back by one of the stepper motors 45. The vacuum in the piston chamber causes the diaphragm membrane covering the pump chamber on the cassette to be sucked flush against the spherical surface of the piston head. The diaphragm is exposed to the vacuum approximately −500 millimeters of mercury in the piston chamber by way of the annular space surrounding the circumference of the piston head where it comes closest to the cylindrical wall of the piston cylinder 55. The periphery of the diaphragm remains sealed airtight against the cassette deck 26 because of the pressurized door due to its inflatable pad. Thus the vacuum in the piston chamber is bounded by the cylindrical wall, the cassette diaphragm and the piston itself. Thus when the piston head retracts, the vacuum continues to hold the diaphragm against the mushroom head and the diaphragm retracts with the piston to thus enlarge the chamber, drawing fluid into one of the chambers A or B of the cassette 34 through whichever valve is opened.

For draining fluids from the patient, an alternating pumping method is employed where one pump 44 extends while the other retracts. When the pump associated with chamber A is extending, the fluid in the chamber A is pushed out into a drain line of the cassette 28. As the pump associated with chamber B retracts, fluid from the patient is drawn into chamber B. When this motion is completed, the pump associated with chamber A then retracts and draws fluid from patient while pump B protracts and transfers fluids out into the drain line. This process continues until the required volume of fluid from the patient is processed.

Initially, the pumps 44 are moved to a home position which is sensed by a conventional optical sensor, not shown. The pump controller encoder value is then set to zero. Next the pump is moved towards the cassette until it touches the cassette. This is the "OUT" position where the encoder is then set to a current encoder value less a maximum (calculated to be the maximum possible stroke, for example, an encoder count of 250). Then, the pump is moved backwards by 800 microsteps, or about an encoder count of 16000. The "HOME" position is then set to this encoder value. The stepper motor 45 next moves backward another 500 microsteps, or about an encoder count of 10,000. This is where the "IN" position is set.

Volume calculation is based on the fact that the cassette volume is a known value (based on its physical dimensions). The volume of the pump head is also a known value (again, the calculation of this volume is based on the physical dimensions of the pump head and chamber). If the whole mushroom head 32 is flushed against the cassette wall 46, then no fluid volume can reside in the cassette chamber. As the mushroom head 32 is moved back, however, it draws fluid into the chamber of the cassette 28 (FIG. 4). The volume of fluid drawn into the chamber is calculated by subtracting the volume of the mushroom head 32 that remains in the chamber from the volume of the chamber. To calculate how much volume of the pump head resides inside the chamber, the amount of linear travel of the pump is calculated, and this distance correlates to the distance of travel of the mushroom head. From that distance a formula is used to determine how much fluid volume still resides in the chamber.

The Electronic Controls for the Pump

Figure 6:
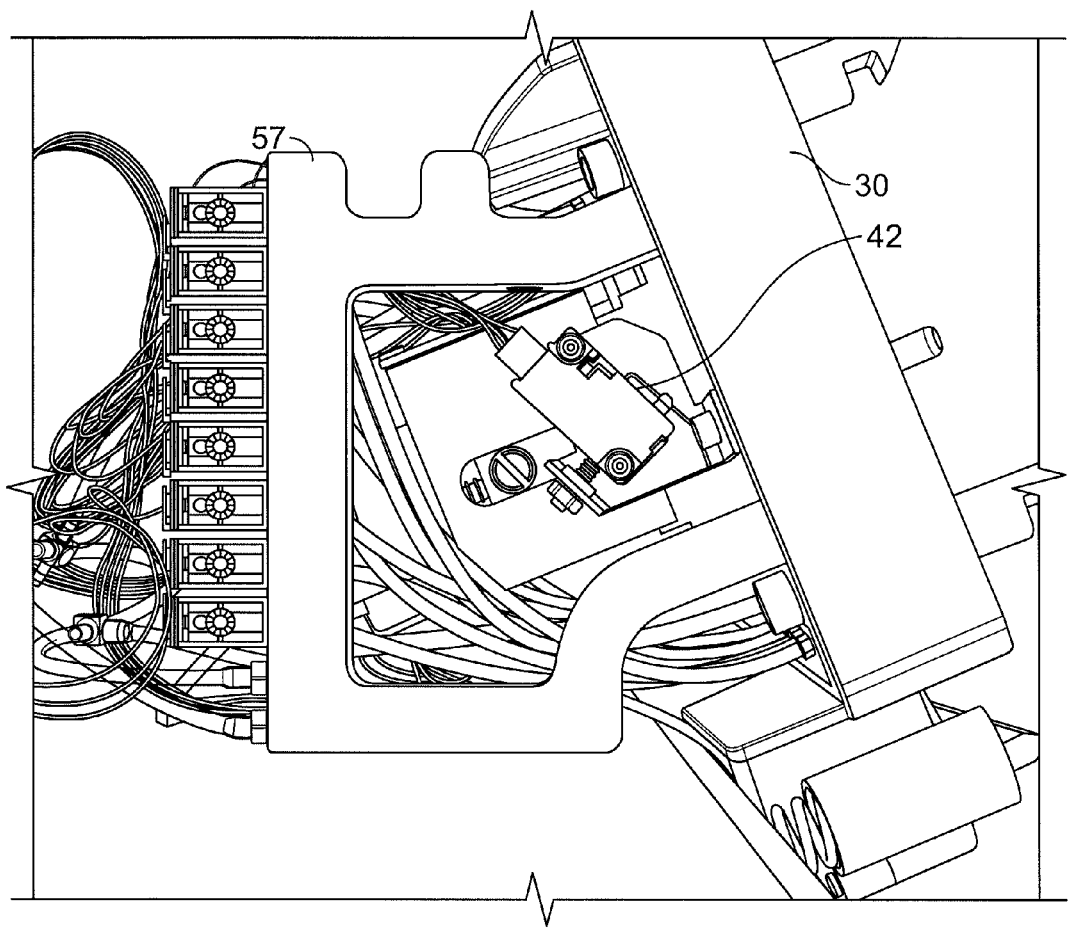

The electronics board 101 of the PD apparatus of the invention is shown in FIG. 6. Stepper motor 100, which drives each pump of the PD apparatus of the invention, is controlled conventionally using firmware with signals to stepper motor driver 108. The firmware resides in two flash memories 102 and 104. The firmware stored in flash memory 102 is used to program the bridge field-programmable gate array (FPGA) 106. The firmware stored in the flash memory 104 is used to program the MPC823 PowerPC microprocessor 112.

Referring to FIG. 2, a stepper motor 45 drives a conventional lead screw (not shown) which moves a nut (also not shown) in and out on the lead screw. The nut, in turn, is connected to a mushroom head 32 which actually makes contact with the membrane A or B on the cassette 28 (FIG. 4). The stepper motor and lead screw are chosen to provide the required force to push fluid out of the cassette following the opening of fluid paths in cassette, as will be described later. The stepper motor 45 preferably requires 200 steps to make a full rotation, and this corresponds to 0.048" of linear travel. Additionally, an encoder measures the angular movement of the lead screw. This measurement can be used to very accurately position the mushroom head assembly.

A stepper motor controller (not shown) provides the necessary current to be driven through the windings of the stepper motor. The polarity of the current determines whether the head is moving forward or backward. Rough positioning of the piston is aided by one or more opto-sensors (not shown).

Inside the FPGA 106, there are two duplicate sets of control logic, one for each piston. The two-channel quadrature output of the linear encoder 110 (FIG. 6) is converted into an increasing or decreasing count. The overall range of this count is from 0 to ~65,000 (or, the count can be split in half about 0, from −32,499 to +32,500). This count is required to determine the current position and subsequent movement of the piston. There is a direct correlation between actual movement of the lead screw and an encoder value.

Referring again to FIG. 6, the FPGA 106 makes a comparison between the current encoder input and a target value. This is needed for automatic movement. A single command to the FPGA 106 initiates a complete cycle that ends with the piston being moved from its current position to newly designated position. Additionally, the FPGA 106 can automatically stop the motor movement. This is desirable, for example, where the pump head reaches its end of travel (sensed by end of travel switch 112, or where the pumping action causes the pressure to be out-of-bounds. If the piston reaches an end-of-travel switch 112, the automatic movement is halted. Likewise, if a pressure sensor 48 (FIG. 2) determines that the pressure is outside of the prescribed, limited range, the motors 45 (FIG. 2) can be halted to prevent a larger excursion, which might be harmful to the patient.

Another part of the FPGA firmware allows the speed of the stepper motors 45 to be controlled, as is well known in the art. By adjusting the motor pulse duration and time between pulses, the motor can run faster or slower to get a desired speed vs. torque balance. The speed the motor runs is inversely related to the torque it is able to apply to the pump head. This adjustment allows the machine to produce the desired amount of push on the fluid in the pump chambers A or B (FIG. 4) so that it flows easily through the lines, but isn't forced so as to trigger pressure alarms or cause rupture of the lines. On the other hand, if you try to run the motor too fast, you may lose the necessary torque required on the pump head to move the fluid through the line.

In addition to the motor pulse, the FPGA 106 provides several control signals to the stepper motor controllers (not shown), for example, direction and step size. Depending on the values sent from the flash memories 102 and 104 to the FPGA 106, the step size can be adjusted between full, half, quarter and eighth steps. Also, the motor controller can be sent a continuous sequence of pulses for rapid motor movement, or just a single pulse to make a single step. This is set conventionally by registers in the FPGA 106.

The Cassette

The cassette itself is shown in more detail in FIG. 11. The cassette is a biocompatible plastic molded part which has a rigid plastic back facing away from the viewer in FIG. 11. The side that faces the cassette deck as shown in FIG. 11 includes channels and small dome shaped flexible pod like diaphragms forming occludable valves numbered 1 through 16. The intermediate size dome shaped diaphragms cover the pressure sensor chambers P on the cassette facing the deck 26, and finally two large flexible diaphragms cover the clamshell (when expanded) shaped pumping chambers A and B. The diaphragms are facing the viewer in FIG. 11 but would be flush against the piston heads and other mating components of the cassette deck when installed in the cycler. The inlet/outlet valves across the bottom of the cassette are from right to left as follows:

| | |
|---|---|
| 6 | Patient line |
| 7 | N/A (pediatric option) |
| 11 | Solution bag No. 1 |
| 12 | Solution bag No. 2 |
| 13 | Solution bag No. 3 |
| 14 | Last solution bag |
| 15 | Heater bag |
| 10 | Drain |
| A | Pump chamber |
| B | Pump chamber |
| P | Sensors |

Figure 11A:
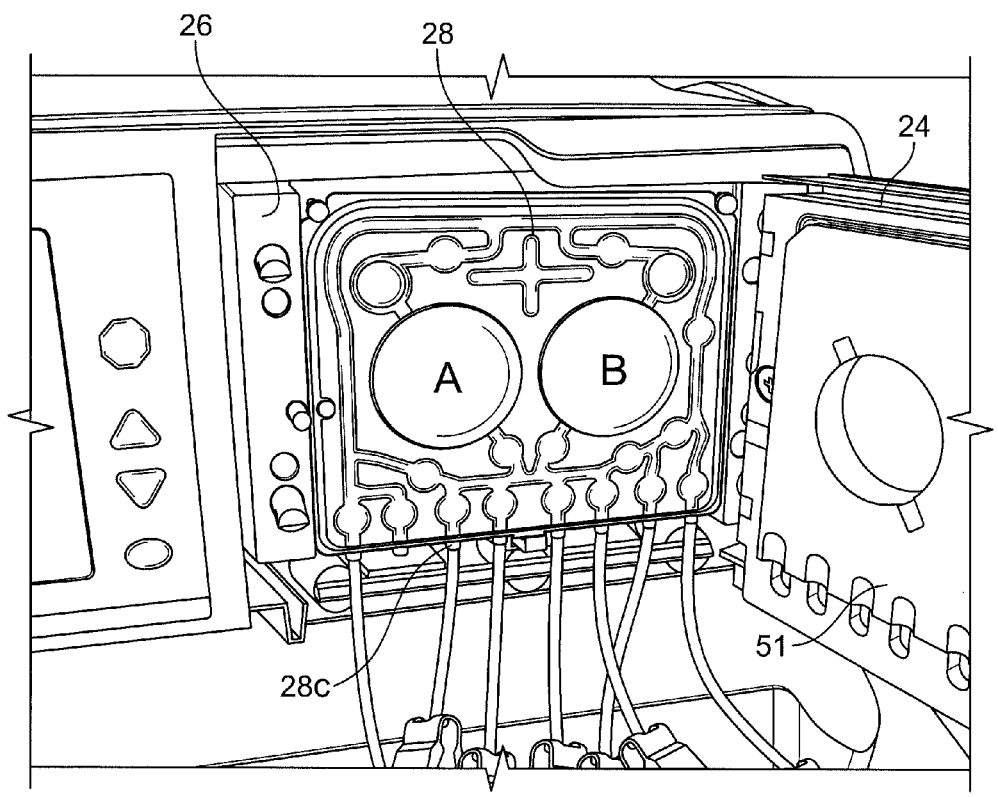
FIG. 11A is a perspective view like those of FIGS. 10A and 10B, but showing a cassette installed in the cassette compartment before closing the door.

The cassette 28 is shown installed in FIG. 11A with its rigid plastic back now facing the viewer and the lines reversed. The inlets and outlets as shown in FIG. 11A are formed with capsule like connectors 28C that allow connection to the tubing set. The connectors 28C project out of the plane of the cassette 28 and fit into mating recesses 51C on the door plate 51, as shown in FIG. 11A. Also shown in FIG. 11A is the safety clamp 71 also shown in FIGS. 4 and 7B. The clamp acts to close all of the inlet/outlet connections in an error situation as described in the description of the pneumatic system below.

Figure 12:
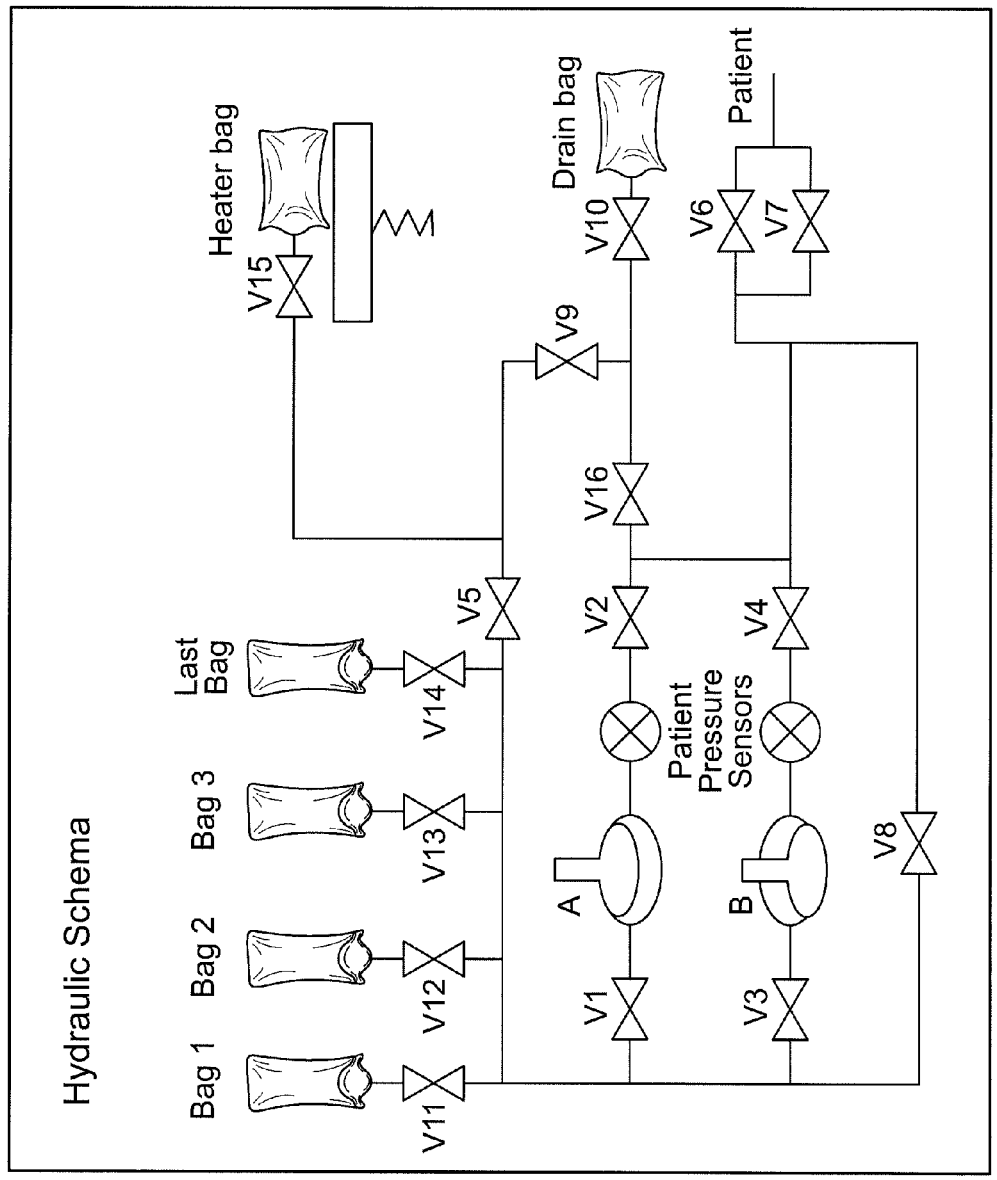
FIG. 12 is a hydraulic schematic for the liquid lines of the cassette and tubing for the cycler of FIG. 2, indicating the valves by number on the cassette of FIG. 11.

The valves in the cassette control and route the flow of PD solution throughout the PD system under the control of a hydraulic network shown in FIG. 12. The valves are designated V1-V16 and correspond to the numbered valves in FIG. 11. The flow lines in the schematic are implemented by the cassette's preformed channels. The valves are actuated pneumatically to case various sources and destinations to be placed in fluid communication. For example, for fluid to flow from Bag 1 (one of the bags 18 hanging on the cart 12 in FIG. 2), valve V11 is opened and pump valve V1 is opened while the piston head for chamber A is retracting to fill the chamber, then V1 is closed and V2, V16, V9 and V15 are opened while the piston head 32 protracts into the chamber A driving liquid out into the heater bag. Other examples are shown in FIGS. 13A, 13B and 13C.

One other design feature of the cassette 28 which is not found in other cassettes is the circumferential channel 28D formed in the cassette. Channel 28D actually circumnavigates the entire periphery of the cassette passing valves 16, 9, 5 and 8. This channel also passes by all of the inlet/outlet ports on the bottom of the cassette. Thus the interconnected circumferential channel 28D has multiple uses in delivering fluid to and from the pump chambers A and B. This arrangement also potentially affords an opportunity for flushing the all of the lines of the cassette by appropriate valve openings. For example, fluid could be introduced under pressure from the drain outlet 10 and forced all the way around the cassette and out the rest of the ports 6, 7 and 11-15.

Description of Fluid Flow Through the Machine

Figure 13A:
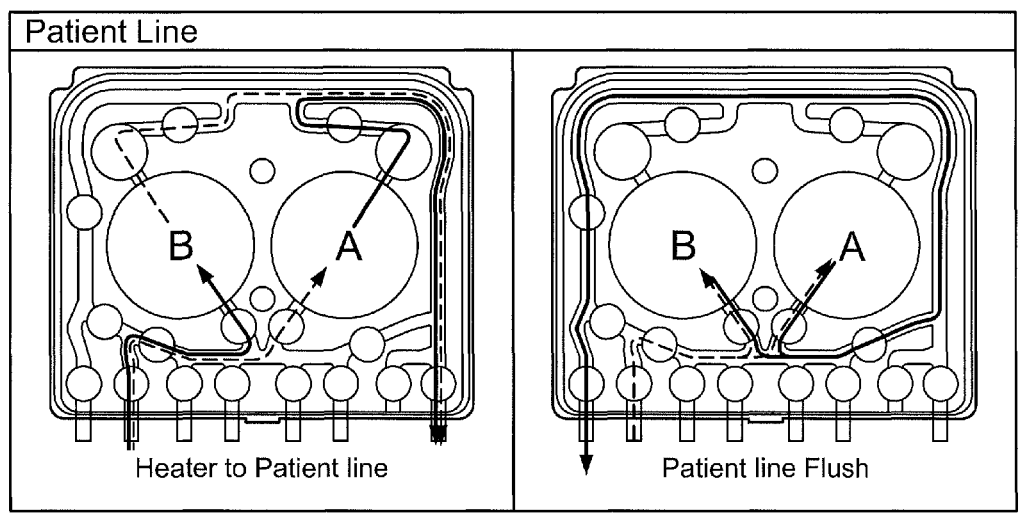
FIGS. 13A, 13B and 13C illustrate various PD solution flow paths through the cassette of FIG. 11.
Figure 13B:
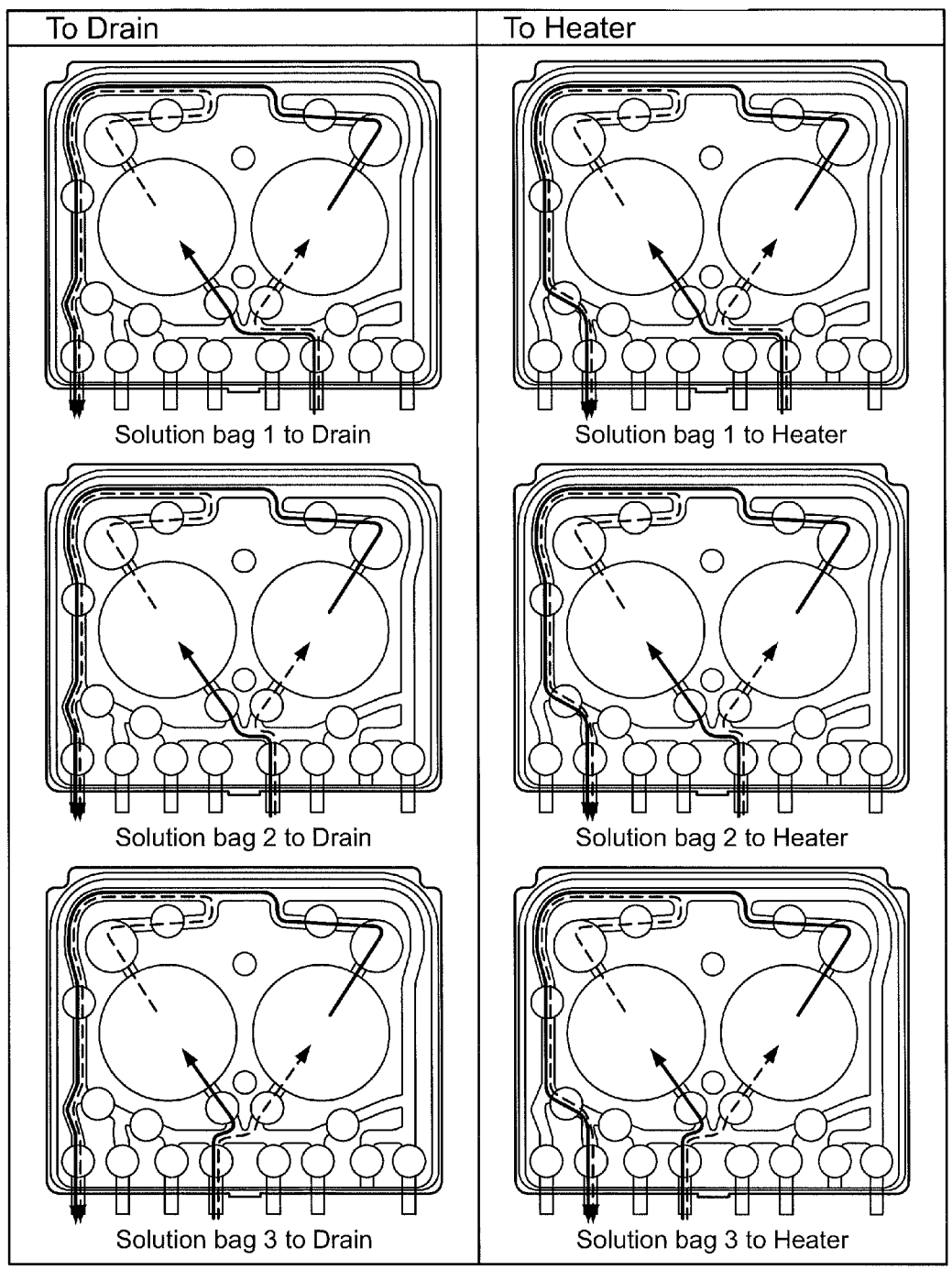
Figure 13C:
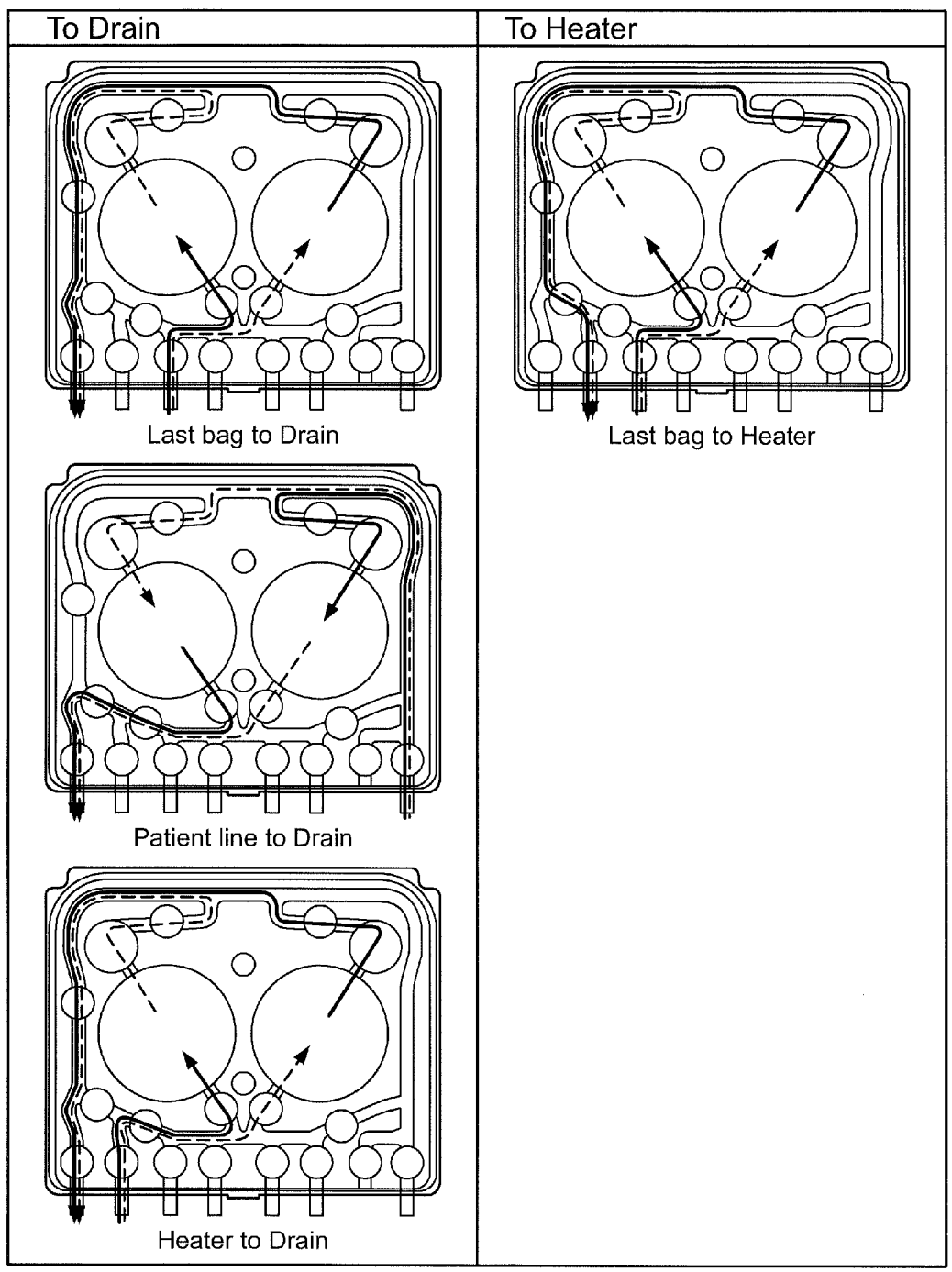

The fluid flow through the disposable cassette 28 is illustrated in FIGS. 13A-13C. The PD machines of the invention utilize six fluid-processing sequences: flush, prime, drain, fill, pause and dwell. The purpose of the flush sequence is to remove air from all the lines (except the patient line) and from the cassette. This is accomplished by pumping dialysate solution through the lines to be flushed.

The prime sequence removes air from the patient line by pumping dialysate solution through the patient line. The drain sequence is used to pump dialysate solution from the patient to the drain. The fill sequence is used to pump dialysate solution from the heater bag to the patient. The pause sequence allows the patient to disconnect from the PD machine once the patient has been filled with dialysate solution. While the patient is disconnected from the machine, the machine will be transferring dialysate solution from the solution bags to the heater bag. Finally, the dwell sequence is used to allow the dialysate solution to remain for a set time in the patient. Dwell sequences are identical to pause sequences with the exception that the patient does not disconnect from the machine. While a dwell sequence is occurring, the machine will be transferring dialysate solution from the solution bags to the heater bag.

Each figure contains a dashed or solid line, each line having arrows that indicate the direction of flow. All flow diagram lines that are the same pattern (i.e., either dashed or solid) occur at the same time during the process. The different line patterns thus represent alternate times.

For example in FIG. 13A, in the "Heater to Patient" line diagram, when pump chamber A is filling, chamber B is emptying. The dashed lines indicate that pump A is retracting to pull dialysate solution from the heater bag. At the same time pump B is protracting to pump dialysate solution through the patient line. The solid lines indicate that pump A is protracting to push dialysate solution to the patient. At the same time, pump B is retracting and pulling dialysate solution from the heater bag.

FIGS. 13B and 13C show more of the flush sequence as the dialysate solution comes from the supply and moves through the drain line.

FIG. 13A illustrates the prime sequence as the solution from the heater bag pushes air out of the patient line, as well as the fill sequence where solution from the heater bag is pumped to the patient. FIG. 13C illustrates the drain sequence as the solution is pulled from the patient and pumped to the drain.

Solution may be pumped from a solution bag to the heater bag while the patient is disconnected (pause mode) or still connected (dwell mode), as shown in FIGS. 13B and 13C.

Owing to the flexibility of the flow paths that can be created by manipulating the balloon valves in coordination with the pumps, any number of other flow paths can be utilized. One possibility would be to drain fluid from the patient during a portion of the drain operation to lines other than the drain line. For example, The patient line could be connected for a period of time during the drain mode to divert some of the spent PD solution from the patient line into one of the empty solution bags to collect a sample for testing.

The Pneumatic System

Figure 14:
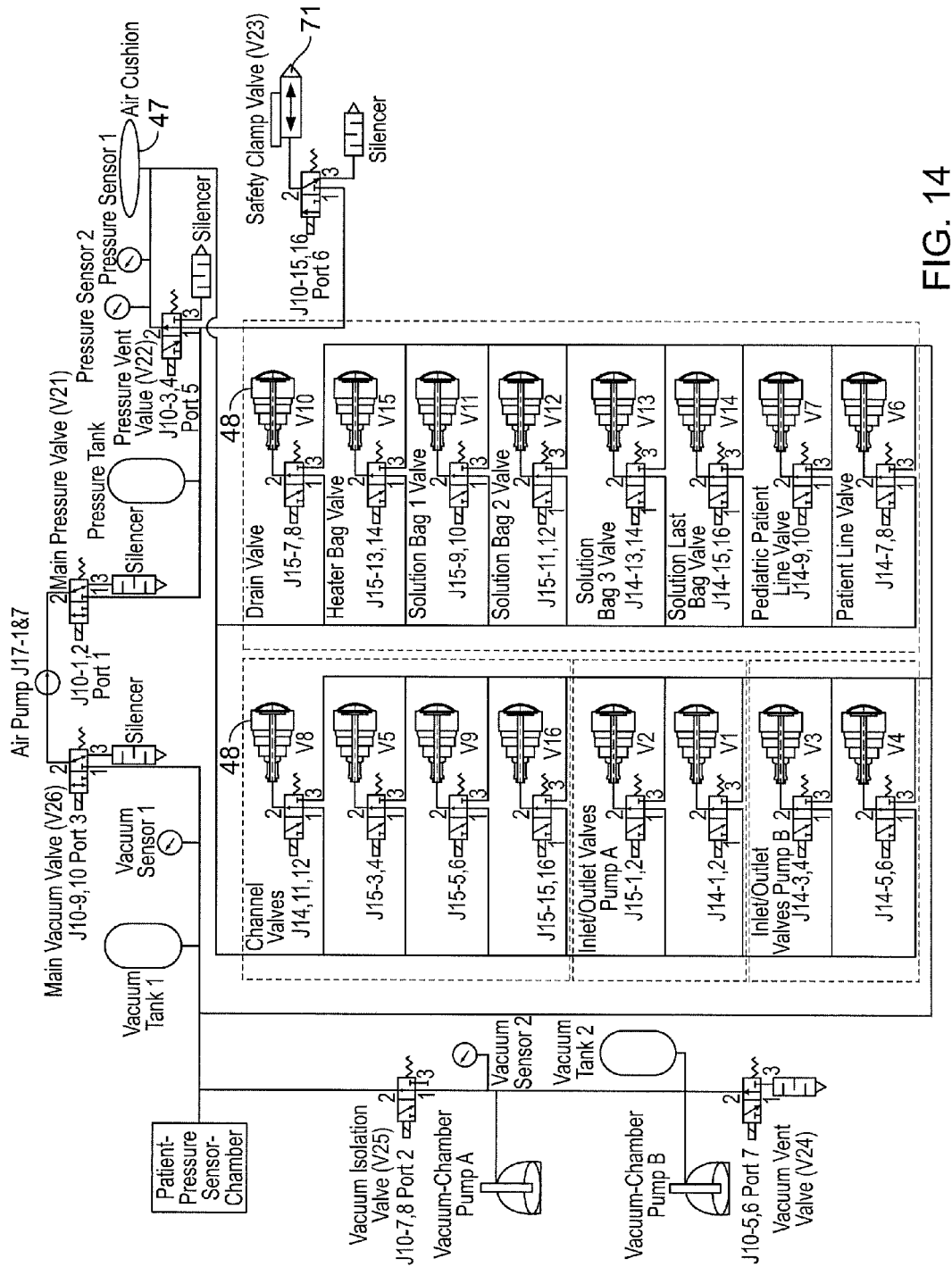
FIG. 14 is a pneumatic schematic for the pressure and vacuum sides of the system for actuating the cassette valves and other pneumatic components of the cycler of FIGS. 1 and 2.
Figure 15:
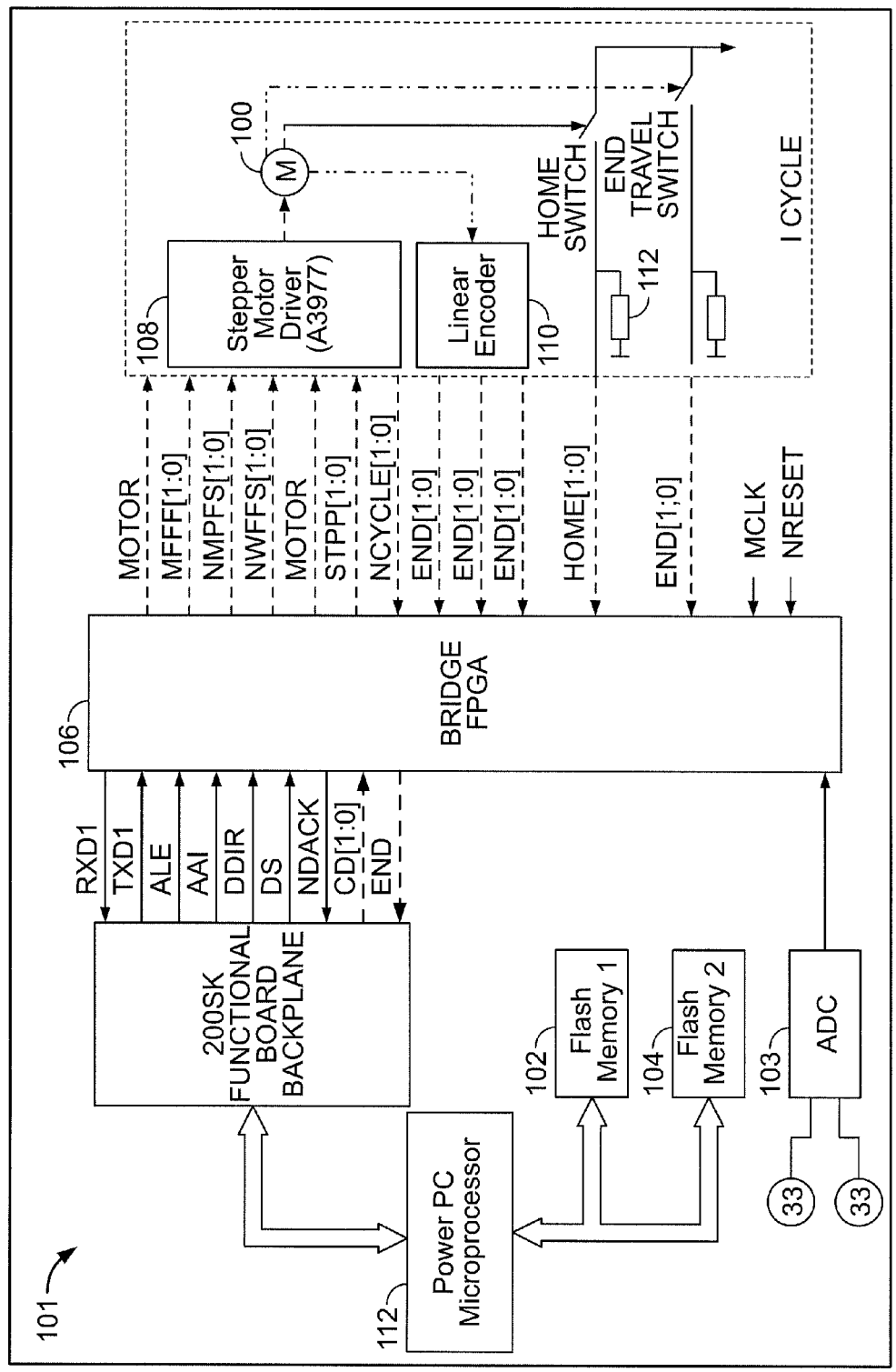
FIG. 15 is a schematic and block diagram of the electronic operation of the PD cycler of FIGS. 1 and 2.
Figure 16:
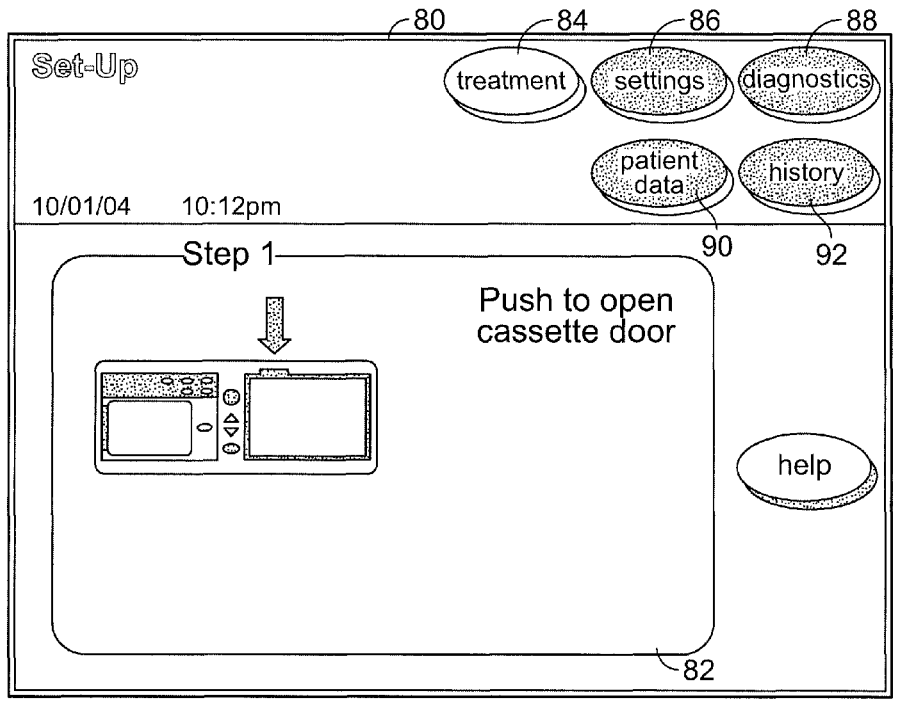
FIGS. 16 and 17 illustrate aspects of the user interface.
Figure 17:
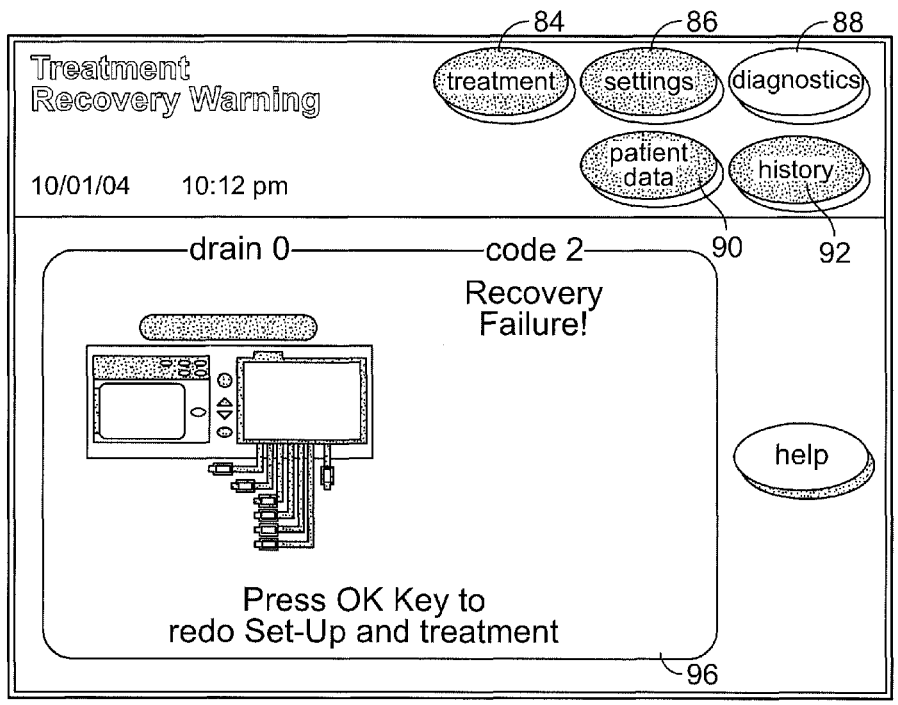

Referring to FIGS. 4 and 14, a pneumatic system provides pressure to operate the valves and fill the inflatable pad 47 to seal the door closed and vacuum to seal the flexible cassette diaphragms to the mating members on the cassette deck 26, namely the mushroom heads and pressure sensors. The basic schematic for the components of the pneumatic system are shown in FIG. 14. A compressor pump is used to provide either air or a vacuum in corresponding reservoirs. On the right side of FIG. 14 as shown, is the pressure tank which is drawn on as necessary to pressurize and maintain the pressure in the inflatable pad 47. During the pumping sequence, this air and vacuum resource is used to inflate and deflate the balloon valves 48. When inflated, a balloon valve will block the fluid from moving through the particular one of channels 1-16 (FIG. 4) of the cassette that mates with the selected one of balloon valves 48. When a balloon valve is deflated, the fluid can move freely through that particular channel controlled by that balloon valve.

Figure 7B:
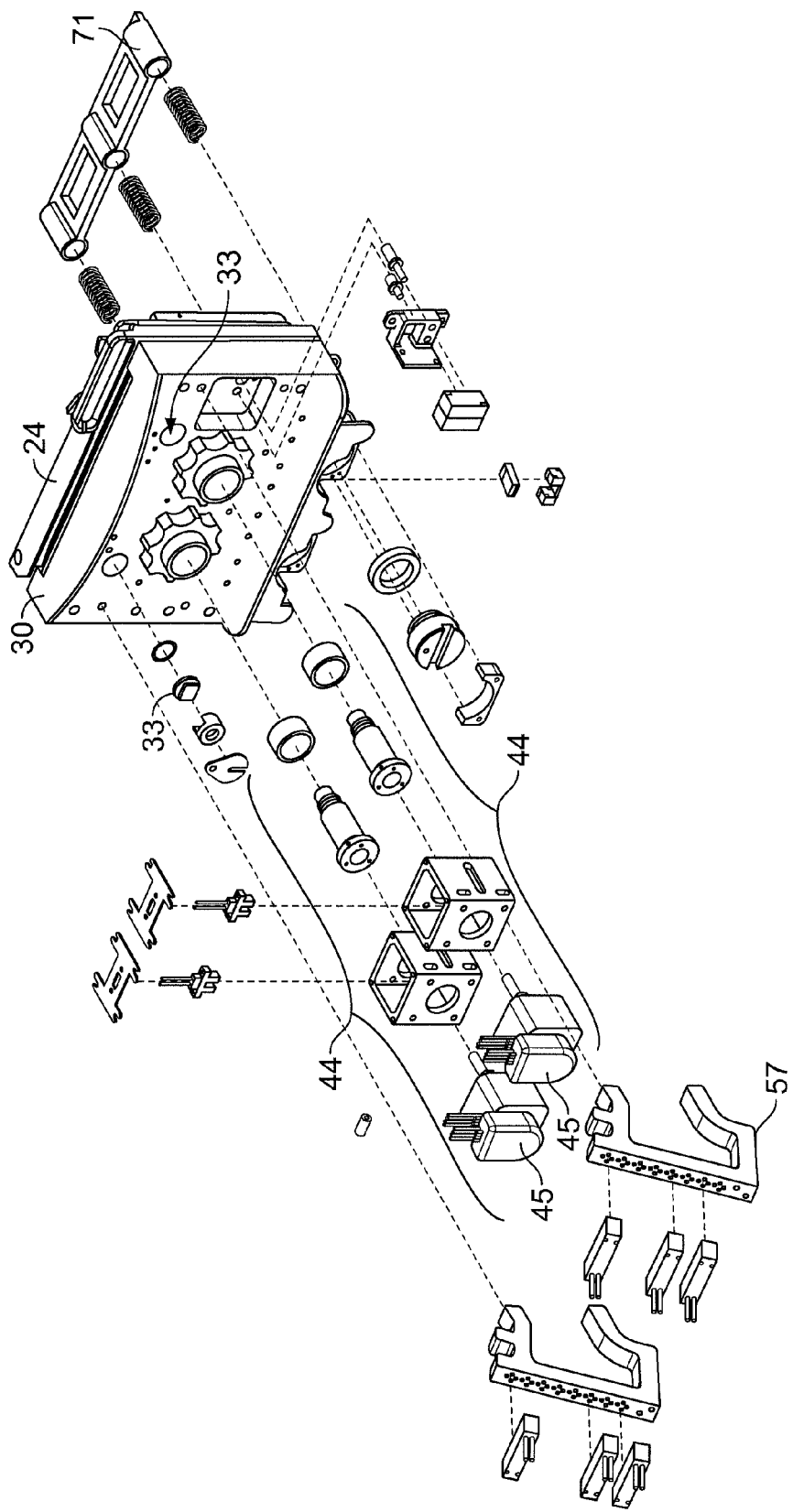

Another function of the pneumatic system is to pressurize the safety clamp 71 shown in FIGS. 4, 11A and 7B. As shown in FIG. 7B, the bar shaped clamp below the cassette deck is spring loaded and acts like a "dead-man" brake switch. Pneumatic pistons operated by the pneumatic system retract the clamp against the spring force when pressurized thus withdrawing the clamp 71 away from the door 24. As shown in FIG. 11A, the clamp extends across all of the tubing connected to the cassette and in the absence of pressure will crimp closed all seven of the tubes shown in FIG. 11A against the bottom of plate 51 in the door 24. This happens automatically when the machine's controller senses some out of bounds condition that makes it unsafe to continue the operation, such as over-temperature of the heater bag, or rupture of one of the lines or excessive patient pressure, or loss of power.

The Pressure Sensors

Referring to FIGS. 4 and 11, a very important requirement of the PD apparatus of this invention is the accurate measurement and control of pressure between the fluid reservoirs and the patient. If the pressure on a line to the patient increases above alarm limits, serious harm can be caused to the patient. The PD system itself needs to operate at pressures that far exceed the limit. These high pressures are needed for to operate the pressure sensors, balloon valves and other functions in the cassette. Therefore these pressures need to be kept independent from the pressures seen by the patient. Appropriate and reliable sealing and valving needs to be used to keep these high pressures away from the patient.

Referring to FIG. 4, to monitor the pressure in the system, two pressure sensors 33 are utilized to indirectly detect the pressure and vacuum within the patient's peritoneum. These sensors are preferably solid state silicon diaphragm infusion pump force/pressure transducers, for example Model 1865 made by Sensym Foxboro ICT. When cassette 28 (FIG. 4) is inserted into the cassette compartment 60, the pressure sensing areas "P" within the cassette 28 (FIG. 11) line up and are in intimate contact with the two pressure sensors 33. These sensing areas P are connected, respectively, directly to each chamber A and B through canals 62 and 64, respectively, so that when fluid moves in and out of the chambers A and B, the pressure sensors 33 can detect its presence. The cassette membrane comprising two areas marked "P" adheres to the pressure sensors 33 using vacuum pressure in the same manner as the diaphragms of the pump chambers A and B are sealed against the mushroom head. Clearance around the pressure sensors communicates vacuum to the pressure dome diaphragms the circumferences of which are sealed airtight to the cassette deck by the pressurization of the door compartment.

The two pressure sensors 33 are connected to a high resolution 24 bit Sigma-Delta, serial output A-D converter (ADC) 103 on I/O board 101. This ADC sends a signal from each of the two pressure sensors to the FPGA 106 on the board 101. After the data ready signal is received by the FPGA 106, the FPGA reads this ADC and transfers this data to be processed by the microprocessor 112, which in the preferred embodiment of the invention is an MPC823 PowerPC device manufactured by Motorola, Inc.

On completion of the flush and prime processes, as is well known in the art, the cassette will be filled with solution. At this time, the line to the patient will be completely filled with solution. The pressure at this stage is detected and will be used as base line for static pressure. At that time, the patient's head height relative to the PD machine will be determined from the differential in the pressure reading. Preferably, this pressure differential is maintained below 100 mbar.

During the drain sequence, the maximum pump hydraulic vacuum is limited to −100 mbar to prevent injury to the patient. The vacuum in the peritoneum must be held at or above this value. The position of the patient below or above the PD machine level indicated by the static pressure measurement is compensated by adjusting the level of the vacuum.

By way of example, the target vacuum of the vacuum chamber can be based on the following equation:

$$P_{stat} = \text{static hydraulic pressure}(+1 \text{ meter} = +100 \text{ mbar} \text{ and } -1 \text{ meter} = -100 \text{ mbar})$$

$$P_{patmax} = -100 \text{ mbar}$$

$$P_{vac} = \text{target vacuum of vacuum chamber}$$

$$P_{vac} = P_{patmax} + P_{stat}$$

For example, where the patient is 1 meter above the PD machine, the differential pressure=+100 mbar; Pvac=−100 mbar+100 mbar=0 mbar.

Where the patient on same level than machine, the differential pressure=0 mbar;

$$P_{vac} = -100 \text{ mbar} + 0 \text{ mbar} = -100 \text{ mbar.}$$

Where the patient is 1 meter below machine, the differential pressure=−100 mbar;

$$P_{vac} = -100 \text{ mbar} + -100 \text{ mbar} = -200 \text{ mbar.}$$

Since continuous flow through the various lines connected to the patient is essential to proper treatment of the patient, it is important to continuously monitor if a patient line is blocked, partially blocked or open. There are three different possible situations:
1. the patient line is open;
2. the patient line is closed; or
3. the patient line is not completely open and therefore creates an undesired flow resistance (caused, for example by the patient is lying on the line).

The pressure sensors 33 (FIG. 2) can be used to detect error conditions. Referring to FIG. 5A, when the pump B is protracting and thereby pumping dialysate fluid into a line that is open to patient, it is very important that the patient pressure and the encoder values are carefully monitored, using the pressure sensors 33 described above. Three possible error situations may occur, for example, as a result of the following events:
1. The patient line is open when pump B is protracting until a defined length value is reached, and the patient pressure is not increasing;

2. The patient line is closed, and the pump is not able to protract because the patient pressure increases to a defined alarm limit.
3. The pump protracts to produce an increasing patient pressure, but the pressure decreases slowly.

These error conditions may be sensed using the pressure sensors 33 of the invention, and corrective action can then be taken, either automatically or by sending an alarm to the patient, where the screen tells the patient what action to take. For example, the screen may tell the patient that he or she may be lying on a fluid line, and should move off of it.

Since the patient pressure sensors are critical components to patient safety, it is very important to monitor whether these sensors are functioning properly. Although prior machines have attempted to accomplish this monitoring by checking the pressure readings from the sensors, such tests are not foolproof, because the varied nature of the normal, expected readings may fool one to believe that the sensors are working properly when actually they are not.

Therefore this sensor monitoring should be independent of the pressure measurements. In a preferred embodiment of the invention, the pressure sensors are monitored through an A-to-D converter ("ADC") having two dedicated current sources, one for each sensor. On command, each ADC will source current (instead of acquiring data, as is usual case) and monitor how this current flows (or fails to flow) through each sensor. This independent monitoring of the pressure sensors would guarantee patient safety. Since normal treatments typically run overnight, the ability to continually double-check the very pressure sensors that monitor patient safety is indeed desirable.

The User Interface

One important part of a patient-controlled PD machine is the user interface, shown in FIG. 7. A common problem with prior art machines is that the patient loses track of the mode in which the machine is operating. In the invention, the touch screen display has at least two portions: one is a mode-indicating portion 80, and the other is an operation descriptive portion 82.

The mode-indicating portion 80 has a plurality of touch sensitive indicia 84, 86, 88, 90, and 92, each indicating the mode in which the machine is operating to keep the patient continually informed of which one of at least three operating modes the machine is operating in. These modes as illustrated in the preferred embodiment shown in FIG. 7. By way of example and not of limitation, the modes may include: a treatment mode 84, during which dialysis is taking place; a settings mode 86, where the treatment type settings of the PD machine are displayed and can be modified by the patient; a diagnostic mode 88 where the operation of the machine is being diagnosed; a patient data mode 90, where patient data is displayed; and treatment history mode 92, where prior treatment of the patient is displayed.

During operation under any of these modes, the operation descriptive portion 82 of the display changes to display details of the specific operation being carried out within the selected mode. Generally, the descriptive portion shows helpful information to guide the user in operating the machine. For example, during treatment, when the treatment mode indicator is highlighted, as shown in FIG. 7, the descriptive portion 82 shows the patient that the next required step is to "Push open cassette door." Alternatively, the descriptive portion may show the direction of fluid flow, or provide an indication of the extent of treatment completion or other description of the current stage of treatment. The same kind of descriptions is provided for various diagnostic operations which take place in the diagnostic mode.

All five illustrated mode indicia in the mode portion 80 of the screen, for each of the five operating modes of the preferred embodiment, always remain visible to the patient, with the mode that the machine is currently operating in being highlighted in some manner, as shown in FIG. 7 for the treatment mode indicator 84.

The operating mode is changed by the patient by touching one of the indicia on the screen different from the one ("treatment" in FIG. 7) that is currently highlighted. Unless there is some reason, such as safety or otherwise, that the mode must not be changed at that time, the mode will change to the new mode when the patient touches the different icon, and the newly selected icon 88, "diagnostics" as shown in FIG. 8, will be highlighted and the "treatment" icon 84 for the prior operating mode will no longer be highlighted, as shown in FIG. 8.

Figure 8:
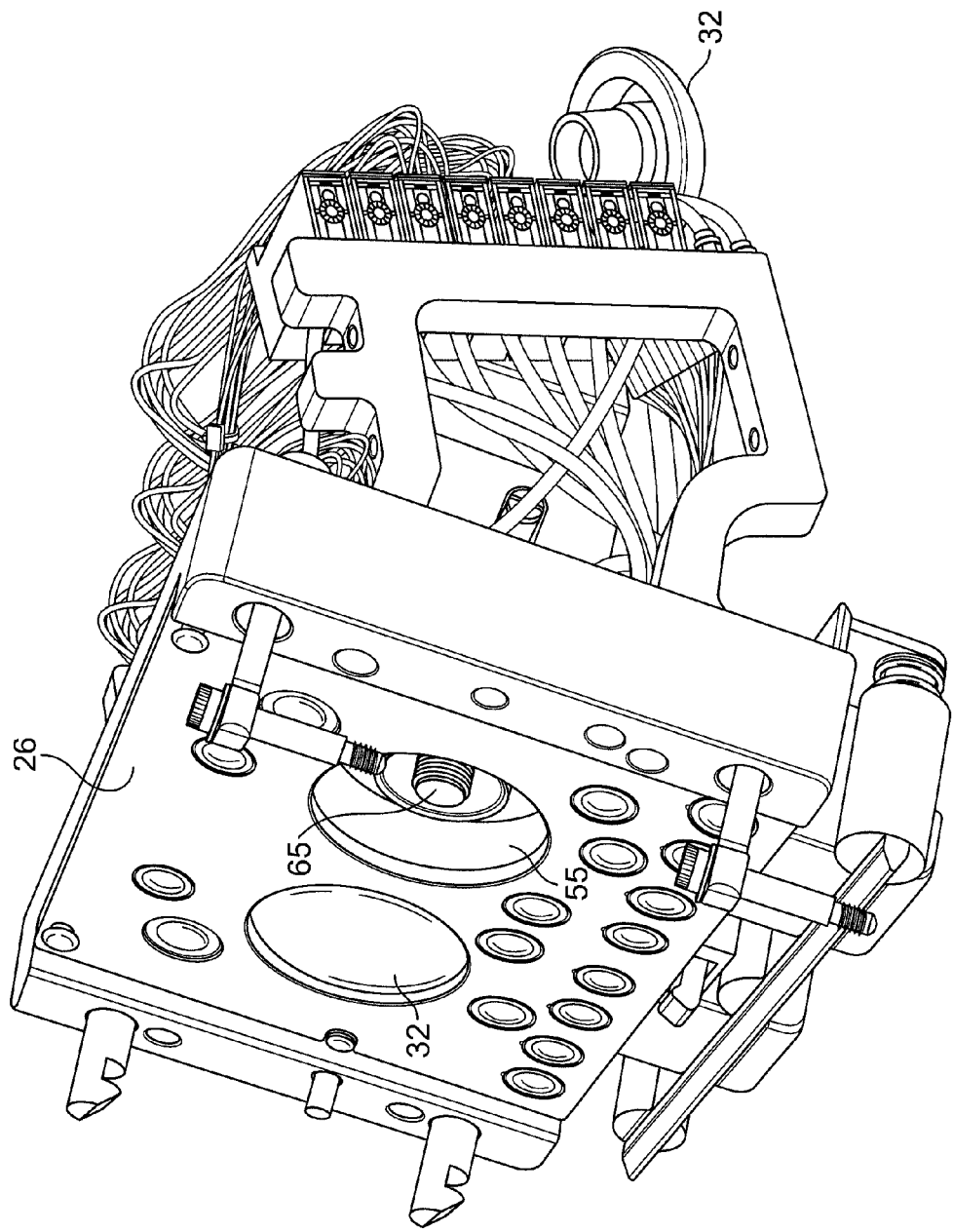
FIG. 8 is a perspective view of the front of the cassette deck of FIGS. 5 and 6.

Then the descriptive portion 96 of the touch screen, shown in FIG. 8, will display information pertaining to the new "diagnostics" mode of operation, such as a "treatment recovery warning" shown in FIG. 8. Icons 84, 86, 90 and 92 for all the other four possible modes in the preferred embodiment will remain displayed, but not highlighted, so the patient always knows (1) what mode the machine is operating in; and (2) what other possible operating modes exist.

The invention has been described in terms of particular embodiments. Other embodiments are within the scope of the following claims. For example, steps of the invention can be performed in a different order and still achieve desirable results.

What is claimed is:

1. A peritoneal dialysis (PD) system comprising:
   a disposable PD cassette comprising
      a base having a substantially planar portion and a dome-shaped protrusion extending from the substantially planar portion, the dome-shaped protrusion defining a recessed region,
      a flexible membrane attached to the base and covering the recessed region of the dome-shaped protrusion to form a pumping chamber between the flexible membrane and the recessed region of the dome-shaped protrusion, and
      a plurality of tubing connectors positioned along one edge of the PD cassette; and
   a PD machine comprising
      a deck having a plurality of openings,
      a door hinged from one side to the deck, the door and the deck being arranged so that when the door is closed over the deck, the door and the deck cooperate to form a cassette compartment configured to receive the disposable PD cassette therein, and the door having a cylindrical recess positioned to receive the dome-shaped protrusion of the base of the disposable PD cassette when the disposable PD cassette is disposed in the cassette compartment of the PD machine with the door closed,
      a piston head at least partially disposed within one of the openings of the deck, the piston head being aligned with the pumping chamber of the disposable PD cassette when the disposable PD cassette is disposed in the cassette compartment of the PD machine, and
      an inflatable bladder configured to compress the substantially planar portion of the base of the disposable PD cassette between the deck and the door of the PD machine when the disposable PD cassette is disposed in the cassette compartment of the PD machine with the door closed and the inflatable bladder is inflated.

2. The PD system of claim 1, wherein when the PD machine is resting on a substantially horizontal surface during use, the deck lies in a plane inclined from the vertical by 10 to 35 degrees.

3. The PD system of claim 2, wherein when the cassette is disposed in the cassette compartment, all of the tubing connectors are in a line along a bottom edge of the cassette so that tubes connected to the tubing connectors bend between the cassette and the substantially horizontal surface on which the PD machine is resting, at an angle greater than 90 degrees.

4. The PD system of claim 3, wherein the tubing connectors extend beneath the door of the PD machine.

5. The PD system of claim 1, wherein the cassette defines a circumferential channel that extends along a perimeter region of the cassette, and the circumferential channel can be placed in fluid communication with the pumping chamber.

6. The PD system of claim 1, wherein the piston head is a mushroom-shaped piston head.

7. The PD system of claim 6, wherein the pumping chamber is substantially clamshell shaped.

8. The PD system of claim 1, wherein the PD machine further comprises a clamp that, when the cassette is disposed in the cassette compartment and tubes are connected to the tubing connectors of the cassette, extends across all of the tubes such that all of the tubes can be crimped by the clamp at one time.

9. The PD system of claim 8, wherein the PD machine further comprises a controller that causes the clamp to crimp all of the tubes when a potentially unsafe condition is detected.

10. The PD system of claim 1, wherein the pump chamber has an inlet port and an outlet port.

11. The PD system of claim 1, wherein the PD machine comprises a plurality of inflatable balloon valves positioned in some of the openings in the deck.

12. The PD system of claim 1, wherein the PD machine comprises two piston heads that travel back and forth through two of the openings in the deck when reciprocated, the PD cassette defines two pumping chambers, and the piston heads align with the pumping chambers when the PD cassette is disposed in the cassette compartment of the PD machine.

* * * * *

(12) EX PARTE REEXAMINATION CERTIFICATE (11707th)
United States Patent
Plahey et al.

(10) Number: US 8,784,359 C1
(45) Certificate Issued: Jul. 31, 2020

(54) CASSETTE SYSTEM FOR PERITONEAL DIALYSIS MACHINE

(75) Inventors: Kulwinder S. Plahey, Martinez, CA (US); Frank L. Hedmann, Volkach (DE); Stephan Klatte, Wurzburg (DE); Thomas Irvin Folden, Alamo, CA (US)

(73) Assignee: FRESENIUS MEDICAL CARE HOLDINGS, INC., Lexington, MA (US)

Reexamination Request:
No. 90/014,403, Nov. 1, 2019

Reexamination Certificate for:
Patent No.: 8,784,359
Issued: Jul. 22, 2014
Appl. No.: 13/092,560
Filed: Apr. 22, 2011

Related U.S. Application Data

(63) Continuation of application No. 11/515,359, filed on Aug. 31, 2006, now Pat. No. 7,935,074, which is a continuation-in-part of application No. 11/069,195, filed on Feb. 28, 2005, now abandoned.

(51) Int. Cl.
*A61M 1/28* (2006.01)
*A61M 1/16* (2006.01)

(52) U.S. Cl.
CPC ............... *A61M 1/28* (2013.01); *A61M 1/16* (2013.01); *A61M 1/281* (2014.02); *A61M 1/288* (2014.02); *A61M 2205/122* (2013.01); *A61M 2205/128* (2013.01); *A61M 2205/505* (2013.01)

(58) Field of Classification Search
None
See application file for complete search history.

(56) References Cited

To view the complete listing of prior art documents cited during the proceeding for Reexamination Control Number 90/014,403, please refer to the USPTO's public Patent Application Information Retrieval (PAIR) system under the Display References tab.

*Primary Examiner* — Jeffrey R Jastrzab

(57) ABSTRACT

A peritoneal dialysis (PD) system that includes a disposable PD cassette including a base having a substantially planar portion and a dome-shaped protrusion extending from the substantially planar portion and a flexible membrane attached to the base and covering a recessed region of the dome-shaped protrusion to form a pumping chamber between the flexible membrane and the recessed region of the dome-shaped protrusion. The system also includes a PD machine including a deck and a door hinged from one side to the deck. The door and the deck can cooperate to form a cassette compartment, and the door has a cylindrical recess positioned to receive the dome-shaped protrusion of the base of the disposable PD cassette when the disposable PD cassette is disposed in the cassette compartment and the door is closed.

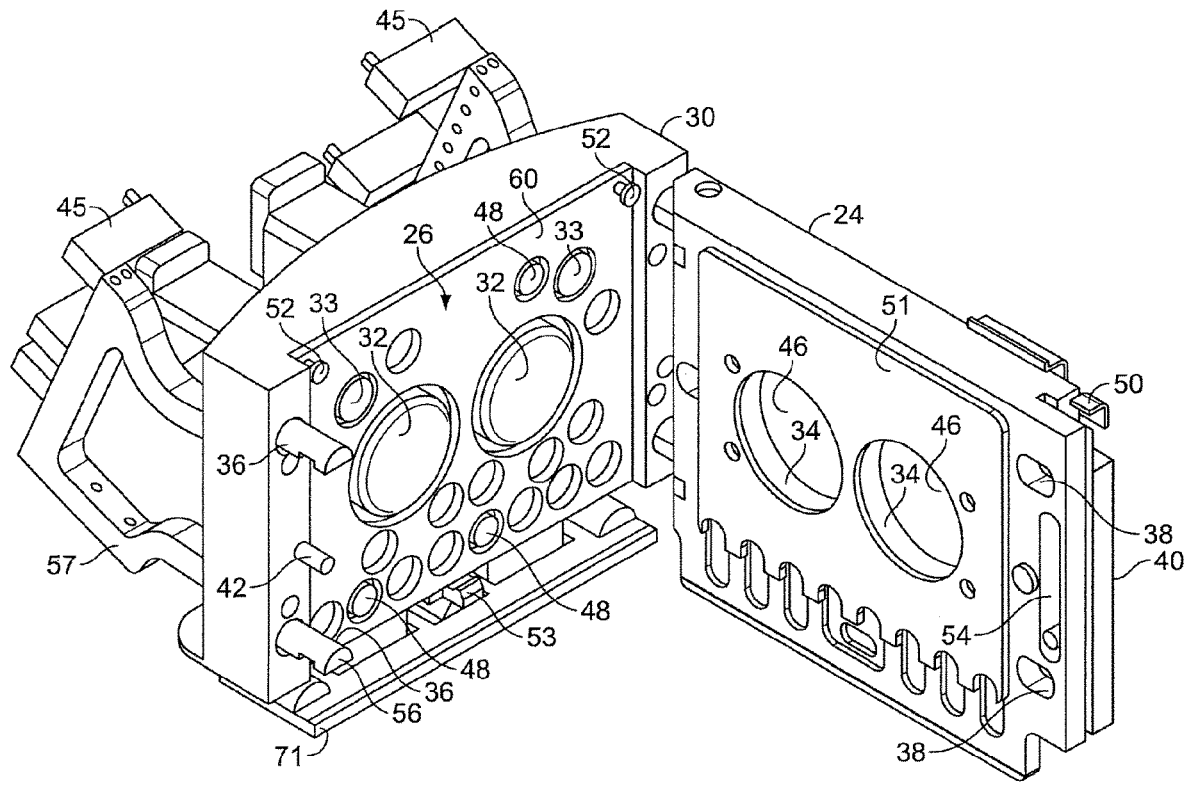

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1 and 5-12 is confirmed.

New claims 13-33 are added and determined to be patentable.

Claims 2-4 were not reexamined.

*13. The PD system of claim 1, wherein the circumferential channel of the cassette has a first portion extending along a first edge of the cassette and a second portion extending along a second edge of the cassette, the first and second edges of the cassette being substantially perpendicular to one another.*

*14. The PD system of claim 13, wherein the first portion of the circumferential channel of the cassette extends along substantially an entire length of the first edge of the cassette.*

*15. The PD system of claim 14, wherein the second portion of the circumferential channel of the cassette extends along substantially an entire length of the second edge of the cassette.*

*16. The PD system of claim 13, wherein the circumferential channel of the cassette circumferential channel has a third portion extending along a third edge of the cassette, the first and third edges of the cassette being substantially perpendicular to the second edge of the cassette.*

*17. The PD system of claim 16, wherein the first portion of the circumferential channel of the cassette extends along substantially an entire length of the first edge of the cassette.*

*18. The PD system of claim 17, wherein the second portion of the circumferential channel of the cassette extends along substantially an entire length of the second edge of the cassette.*

*19. The PD system of claim 18, wherein the third portion of the circumferential channel of the cassette extends along substantially an entire length of the third edge of the cassette.*

*20. The PD system of claim 1, wherein the circumferential channel of the cassette extends about substantially an entire periphery of the cassette.*

*21. The PD system of claim 1, wherein the circumferential channel of the cassette is configured to carry fluid from one of the tubing connectors along the one edge of the cassette around a periphery of the cassette to another one of the tubing connectors along the one edge of the cassette.*

*22. The PD system of claim 21, wherein the circumferential channel can be placed in fluid communication with each of the tubing connectors along the one edge of the cassette.*

*23. The PD system of claim 1, wherein the circumferential channel of the cassette surrounds the pumping chamber of the cassette.*

*24. The PD system of claim 1, wherein the PD cassette defines a second pumping chamber, and the circumferential channel of the cassette surrounds the pumping chambers of the cassette.*

*25. The PD system of claim 1, wherein the circumferential channel of the cassette can be placed in fluid communication with each of the tubing connectors along the one edge of the cassette.*

*26. The PD system of claim 1, wherein the cassette comprises a valve region between the circumferential channel of the cassette and each of the tubing connectors along the one edge of the cassette.*

*27. The PD system of claim 1, wherein the deck defines a cylindrical chamber including the opening in which the piston head is at least partially disposed.*

*28. The PD system of claim 27, wherein an inner diameter of the cylindrical chamber is greater than an outer diameter of the piston head.*

*29. The PD system of claim 28, wherein the piston head is a mushroom-shaped piston head.*

*30. The PD system of claim 1, wherein the dome-shaped protrusion of the PD cassette is rigid.*

*31. The PD system of claim 1, wherein the dome-shaped protrusion of the PD cassette is formed of a rigid biocompatible plastic.*

*32. The PD system of claim 1, wherein the base of the PD cassette is rigid.*

*33. The PD system of claim 1, wherein the base of the PD cassette is formed of a rigid biocompatible plastic.*

\* \* \* \* \*